US010774353B2

(12) United States Patent
Tijani et al.

(10) Patent No.: US 10,774,353 B2
(45) Date of Patent: Sep. 15, 2020

(54) METHODS OF MANUFACTURING THERAPEUTIC PROTEINS

(71) Applicants: MOMENTA PHARMACEUTICALS, INC., Cambridge, MA (US); BIOFACTURA, INC., Frederick, MD (US)

(72) Inventors: Rasheed Tijani, Haverhill, MA (US); Darryl Bacon Sampey, Frederick, MD (US); John Robblee, Concord, MA (US); Gan Wei, Lexington, MA (US); Chaomei He, Wellesley, MA (US)

(73) Assignees: MOMENTA PHARMACEUTICALS, INC., Cambridge, MA (US); BIOFACTURA, INC., Frederick, MD (US)

( * ) Notice: Subject to any disclaimer, the term of this patent is extended or adjusted under 35 U.S.C. 154(b) by 40 days.

(21) Appl. No.: 15/570,178

(22) PCT Filed: Apr. 27, 2016

(86) PCT No.: PCT/US2016/029472
§ 371 (c)(1),
(2) Date: Oct. 27, 2017

(87) PCT Pub. No.: WO2016/176275
PCT Pub. Date: Nov. 3, 2016

(65) Prior Publication Data

US 2018/0135090 A1 May 17, 2018

Related U.S. Application Data

(60) Provisional application No. 62/153,178, filed on Apr. 27, 2015.

(51) Int. Cl.
*C12P 21/00* (2006.01)
*C07K 16/00* (2006.01)
*C12P 21/02* (2006.01)

(52) U.S. Cl.
CPC .............. *C12P 21/00* (2013.01); *C07K 16/00* (2013.01); *C12P 21/02* (2013.01); *C12Y 101/0127* (2013.01); *C12Y 603/01002* (2013.01); *C07K 2317/14* (2013.01)

(58) Field of Classification Search
None
See application file for complete search history.

(56) References Cited

U.S. PATENT DOCUMENTS

2010/0028940 A1 2/2010 Branco et al.
2012/0231500 A1 9/2012 Daramola et al.

FOREIGN PATENT DOCUMENTS

JP 2008539792 A 11/2008
WO WO-2006125126 A2 11/2006
WO WO-2013186230 A1 12/2013
WO WO-2013190032 A1 12/2013
WO WO-2016176275 A1 11/2016

OTHER PUBLICATIONS

Brodsky et al, Glycosylation-related genes in NS0 cells are insensitive to moderately elevated ammonium concentrations, Journal of Biotechnology, vol. 187, 78-86, 2014.
Dalton et al., "Over-expression of secreted proteins from mammalian cell lines", Protein Science, vol. 23, 517-525, 2014.
Fan et al., "The use of glutamine synthetase as a selection marker: recent advances in Chines hamster ovary cell line generation processes", Pharmaceutical Bioprocessing, vol. 1, 487-502, 2013.
Li et al., "Generation of a cholesterol-independent, non-GS NS0 cell line through chemical treatment and application for high titer antibody production", Biotechnology and Bioengineering, vol. 109, 1685-1692, 2012.
Sampey, "Development, characterization and optimization of a novel mammalian protein expression system", Dissertation Abstract only, 2022, p. 1; retrieved from the internet: url:https://drum.lib.umd.edu/handle/1903/19298, retrieved on Oct. 30, 2018.
Yu, "Efficient stable cell pool/cell line development for large-scale antibody and protein production", GenScript Presentation paper, 1-34, 2015.

*Primary Examiner* — Kagnew H Gebreyesus
(74) *Attorney, Agent, or Firm* — Wilson Sonsini Goodrich & Rosati

(57) ABSTRACT

Disclosed herein are methods of manufacturing therapeutic proteins.

22 Claims, 16 Drawing Sheets

Specification includes a Sequence Listing.

NCBI Reference Sequence: NP_057455

```
  1 mrkvvlitga ssgiglalck rllaeddelh lclacrnmsk aeavcaalla shptaevtiv
 61 qvdvsnlqsv fraskelkqr fqrldciyln agimpnpqln ikalffglfs rkvihmfsta
121 eglltqgdki tadglqevfe tnvfghfili relepllchs dnpsqliwts srsarksnfs
181 ledfqhskgk epyssskyat dllsvalnrn fnqqglysnv acpgtaltnl tygilppfiw
241 tllmpailll rffanaftlt pyngtealvw lfhqkpesln plikylsatt gfgrnyimtq
301 kmdldedtae kfyqkllele khirvtiqkt dnqarlsgsc l
```

SEQ ID NO. 1

FIG. 2

NCBI Reference Sequence: NM_016371.3

```
   1 gtactctgat tggtgacggg tgaggcggcc cgaaatcgta ggacttccga aagcagcggc
  61 ggcgtttgct tcactgcttg gaagtgtgag tgcgcgaaga tgcgaaaggt ggttttgatc
 121 accggggcta gcagtggcat tggcctggcc ctctgcaagc ggctgctggc ggaagatgat
 181 gagcttcatc tgtgtttggc gtgcaggaac atgagcaagg cagaagctgt ctgtgctgct
 241 ctgctggcct ctcaccccac tgctgaggtc accattgtcc aggtggatgt cagcaacctg
 301 cagtcggtct tccgggcctc caaggaactt aagcaaaggt ttcagagatt agactgtata
 361 tatctaaatg ctgggatcat gcctaatcca caactaaata tcaaagcact tttctttggc
 421 ctcttttcaa gaaaagtgat tcatatgttc tccacagctg aaggcctgct gacccagggt
 481 gataagatca ctgctgatgg acttcaggag gtgtttgaga ccaatgtctt tggccatttt
 541 atcctgattc gggaactgga gcctctcctc tgtcacagtg acaatccatc tcagctcatc
 601 tggacatcat ctcgcagtgc aaggaaatct aatttcagcc tcgaggactt ccagcacagc
 661 aaaggcaagg aaccctacag ctcttccaaa tatgccactg accttttgag tgtggctttg
 721 aacaggaact tcaaccagca gggtctctat tccaatgtgg cctgtccagg tacagcattg
 781 accaatttga catatggaat tctgcctccg tttatatgga cgctgttgat gccggcaata
 841 ttgctacttc gctttttttgc aaatgcattc actttgacac catataatgg aacagaagct
 901 ctggtatggc ttttccacca aaagcctgaa tctctcaatc ctctgatcaa atatctgagt
 961 gccaccactg gctttggaag aaattacatt atgacccaga agatggacct agatgaagac
1021 actgctgaaa aattttatca aaagttactg gaactggaaa agcacattag ggtcactatt
1081 caaaaaacag ataatcaggc caggctcagt ggctcatgcc tataattcca gcactttggg
1141 aggccaaggc agaaggatca cttgagacca ggagttcaag accagcctga gaaacatagt
1201 gagcccttgt ctctacaaaa agaaataaaa ataatagctg ggtgtggtgg catgcgcatg
1261 tagtcccagc tactcagaag gatgaggtgg gaggatctct tgaggctggg aggcagaggt
1321 tgcagtgagc tgagattgtg ccactgcact ccagcctggg tgacagcgag accctgtctc
1381 aaaatatgta tatatttaat atatatataa aaccagagct gacaatgaca ctctggaaca
1441 ttgcatacct tctgtacatt ctggggtaca tggatttcta ctgagttgga taatatgcat
1501 ttgtaataaa ctatgaacta tgaaaaaaaa aaaaaaa
```

SEQ ID NO. 2

FIG. 3

NCBI Reference Sequence: NP_002056.2

```
  1 mttsasshln kgikqvymsl pqgekvqamy iwidgtgegl rcktrtldse pkcveelpew
 61 nfdgsstlqs egsnsdmylv paamfrdpfr kdpnklvlce vfkynrrpae tnlrhtckri
121 mdmvsnqhpw fgmeqeytlm gtdghpfgwp sngfpgpqgp yycgvgadra ygrdiveahy
181 raclyagvki agtnaevmpa qwefqigpce gismgdhlwv arfilhrvce dfgviatfdp
241 kpipgnwnga gchtnfstka mreenglkyi eeaiekl skr hqyhiraydp kggldnarrl
301 tgfhetsnin dfsagvanrs asiriprtvg qekkgyfedr rpsancdpfs vtealirtcl
361 lnetgdepfq ykn
```

SEQ ID NO. 3

FIG. 4

NCBI Reference Sequence: NM_002065.6

```
   1 gtaaaactat tccccgtgaa ggcggcaggg cagaggtcca gggcgggctt tgctgggagc
  61 ctcgggaccc cgggttgggg gccgtggggc ggcacctggc gagctggcgg gtgggcggcg
 121 agccgaggct tcccggcctg gcggcaactc gcccctctgc cctcagccct cccggctccg
 181 ctcccttccc ccacgccgcc ctgcccctcc cccacgcccc tttctctttc tttctttctt
 241 tcccagttcg cttgccccca ccccagcggc gcccgccggg ctcctcgccc aatggccgcg
 301 gggcccggga ccgcatcagc tgatcggccc gggctcctgg ccgctgggag ccaatcaggg
 361 caccgggggc ggccccgggc cgcggataaa gggtgcgggg ctgctggcgg ctctgcagag
 421 tcgagagtgg gagaagagcg gagcgtgtga gcagtactgc ggcctcctct cctctcctaa
 481 cctcgctctc gcggcctagc tttacccgcc cgcctgctcg gcgaccagcg gggatcctcc
 541 cccagccgca agtccacgaa gaaagcaacg aatgaaaatt atgaagacaa cgagaagtca
 601 gactcctccg ggtcgcgctc cagctgcttc ggcttcgtcg cctactctgt gaactccggg
 661 gagagatctc gagtcaagat taagacctta acccaccaac ctgcctgttc ggacaccccc
 721 cgggccggcc gctgtctgtc cccttctcca tcgccctctc ccagaaagct ccggtgcttg
 781 gaccagctag agtctgagaa agaggagagg cgcgaacgcc actccaaaaa gagaagggtt
 841 aaagagggca accctaacga tacgcttgac tttctgtggc tgggaacacc ttccaccatg
 901 accacctcag caagttccca cttaaataaa ggcatcaagc aggtgtacat gtccctgcct
 961 cagggtgaga aagtccaggc catgtatatc tggatcgatg gtactggaga aggactgcgc
1021 tgcaagaccc ggaccctgga cagtgagccc aagtgtgtgg aagagttgcc tgagtggaat
1081 ttcgatggct ctagtacttt acagtctgag ggttccaaca gtgacatgta tctcgtgcct
1141 gctgccatgt ttcgggaccc cttccgtaag gaccctaaca agctggtgtt atgtgaagtt
1201 ttcaagtaca atcgaaggcc tgcagagacc aatttgaggc acacctgtaa acggataatg
1261 gacatggtga gcaaccagca cccctggttt ggcatggagc aggagtatac cctcatgggg
1321 acagatgggc acccctttgg ttggccttcc aacggcttcc cagggcccca gggtccatat
1381 tactgtggtg tgggagcaga cagagcctat ggcagggaca tcgtggaggc ccattaccgg
1441 gcctgcttgt atgctggagt caagattgcg gggactaatg ccgaggtcat gcctgcccag
1501 tgggaatttc agattggacc ttgtgaagga atcagcatgg gagatcatct ctgggtggcc
1561 cgtttcatct tgcatcgtgt gtgtgaagac tttggagtga tagcaacctt tgatcctaag
1621 cccattcctg ggaactggaa tggtgcaggc tgccatacca acttcagcac caaggccatg
```

FIG. 5A 1681 cgggaggaga atggtctgaa gtacatcgag gaggccattg agaaactaag caagcggcac
1741 cagtaccaca tccgtgccta tgatcccaag ggaggcctgg acaatgcccg acgtctaact
1801 ggattccatg aaacctccaa catcaacgac ttttctgctg gtgtagccaa tcgtagcgcc
1861 agcatacgca ttccccggac tgttggccag gagaagaagg gttactttga agatcgtcgc
1921 ccctctgcca actgcgaccc cttttcggtg acagaagccc tcatccgcac gtgtcttctc
1981 aatgaaaccg gcgatgagcc cttccagtac aaaaattaag tggactagac ctccagctgt
2041 tgagcccctc ctagttcttc atcccactcc aactcttccc cctctcccag ttgtcccgat
2101 tgtaactcaa agggtggaat atcaaggtcg tttttttcat tccatgtgcc cagttaatct
2161 tgctttcttt gtttggctgg gatagagggg tcaagttatt aatttcttca cacctaccct
2221 ccttttttc cctatcactg aagcttttta gtgcattagt ggggaggagg gtggggagac
2281 ataaccactg cttccattta atggggtgca cctgtccaat aggcgtagct atccggacag
2341 agcacgtttg cagaaggggg tctcttcttc caggtagctg aaaggggaag acctgacgta
2401 ctctggttag gttaggactt gccctcgtgg tggaaacttt tcttaaaaag ttataaccaa
2461 cttttctatt aaaagtggga attaggagag aaggtagggg ttgggaatca gagagaatgg
2521 ctttggtctc ttgcttgtgg gactagcctg gcttgggact aaatgccctg ctctgaacac
2581 gaagcttagt ataaactgat ggatatccct accttgaaag aagaaaaggt tcttactgct
2641 tggtccttga tttatcacac aaagcagaat agtattttta tatttaaatg taaagacaaa
2701 aaactatatg tatggttttg tggattatgt gtgttttgct aaaggaaaaa accatccagg
2761 tcacggggca ccaaatttga gacaaatagt cggattagaa ataaagcatc tcattttgag
2821 tagagagcaa gggaagtggt tcttagatgg tgatctggga ttaggccctc aagacccttt
2881 tgggtttctg ccctgcccac cctctggaga aggtgggcac tggattagtt aacagacaac
2941 acgttactag cagtcacttg atctccgtgg ctttggttta aaagacacac ttgtccacat
3001 aggtttagag ataagagttg gctggtcaac ttgagcatgt tactgacaga gggggtattg
3061 gggttatttt ctggtaggaa tagcatgtca ctaaagcagg ccttttgata ttaaattttt
3121 taaaaagcaa aattatagaa gtttagattt taatcaaatt tgtagggttt ctaggtaatt
3181 tttacagaat tgcttgtttg cttcaactgt ctcctacctc tgctcttgga ggagatgggg
3241 acagggctgg agtcaaaaca cttgtaattt tgtatcttga tgtctttgtt aagactgctg
3301 aagaattatt ttttttcttt tataataagg aataaacccc acctttattc cttcatttca
3361 tctaccattt tctggttctt gtgttggctg tggcaggcca gctgtggttt tcttttgcca
3421 tgacaacttc taattgccat gtacagtatg ttcaaagtca aataactcct cattgtaaac
3481 aaactgtgta actgcccaaa gcagcactta taaatcagcc taacataaga tctctctgat
3541 gtgtttgtga ttctttcaaa tccctatgtg ccattatatt tctttatttc ctaaaacagg
3601 caaaataagc tcaagtttat gtactctgag tttttaaaac actggagtga tgttgctgac

FIG. 5B

```
3661 cagccgtttc ctgtacctct ctaagttggg tatttgggac ttaagggatt aagtttttca
3721 cctagactta gttacacaca atcttggcat ttcctagcct agaggtttgt agcagggtac
3781 aagccccact cctcccctt cctttgctcc cctgagtttg gttttggctt accataacat
3841 tgttttgacc attcctagcc taatacaata gcctaacata atgtaagatt aactggcttt
3901 acgatttcta ttctctgctc tcagtgataa gaaacaaata ttagctaccc tgctaccctg
3961 gttgaagcct tccaaggctg gctatgccct aggcatgggc tcatccttgg gtgtatcttg
4021 ccttgcagga agaccagtgg accgattgtg attctcaaaa gctctgtgtt gtcacctgtg
4081 cccttgcccc ttgctcttat cttggtccgt gtatctggga gttcttccac cttatcttgg
4141 ccaattccta ccttcgttca ttcctcatga ggttgggtaa aagctccctc cggctcccat
4201 gatgctgtgc atatacctag caaaaagcaa ttattggaca cattggagtg caatattatt
4261 aatagcatta atactactaa taatgtgggc aatagtgatt gtttttaaaa ggcagtatac
4321 tcttaccagt gcgaggtagc tggggcctgt gatagttttt agagataagt tcttcaggca
4381 actgtgtatt ttacactagt caagtaatcc tagatatccg tggtttttct taagaaagtt
4441 ggctcgtaat atgatttaat attcaaagta gagtcatcta cctattagct tgctggcgtg
4501 gtcctagttt atgcctgttt cagcatgatt gttgagtacc ctgtttcatc cttagcattt
4561 tcttgatttt gttgttaaat gatgtatacc cttatttcca ttgaatctgt gcttccaccc
4621 ccccaactga agttgtcttc cctttgcttg gccaccctta cagcctcttg gatggtgtat
4681 cctacagtgt aagcactaaa ctgaagaggc agtgacctga gcactttgga ttttgttcat
4741 tgtaatcaat tccatgacaa aatgattgca tgagaaggaa ttttaaattc ataggatcag
4801 aatttaggtg aaaacaacca gcatatttgt ttcttcaccc tctcacctag aattagcttt
4861 gacctacagg tcacagtgca atccccttgt atttctaagg tgttttttat agttcatttg
4921 cagacaatgg gttatgtgat aacttttatc agtgatagat taaacagaat aatgaccaag
4981 ctttcaacct taaggagtca ggccagtatt tacaaaagga ggtctccatg aactccttaa
5041 atatgagttc ccctaatatc atcttgccag gtactaaata acaactgata gcacaagcta
5101 tagggaattt gaaagaattc catggatggg tgttgtctag ggccttttgt tgtttttgag
5161 acggggtctg actctcaccc aggctggagt atagtgtggc gcaatcttgg ctcactgcaa
5221 cttctgcctc ccagattcaa gcgattctcc tgcctcagcc tcccaagtag ctgagactac
5281 aggtgtgcac caccatgctc agctaatttt tgtattttta gtacagatgg ggtttcacca
5341 tgttggccag gctggtcttg aactcctgat ctcccaaagt gaggtcttga actggtcttg
5401 aactcctcca cctcccaaag tgctgggatt acaggcgtga gccactgcac ccggcctagg
5461 gccatgtaaa aagccagatc tgtgctgctg tctgtgtaga agggtagaca agtggatgag
5521 aagttcctga actattcttg gccctttttac cactaagtga aagtaacttg ctgccccaaa
```

FIG. 5C

```
5581 gaaagatgtc tcatcattcg acaggacttt ctagttgaac ttcatgaaag caagagatcc
5641 tgtttttctt gctcaccact gtatcttgag acctgttgta gtgcctgcaa tacttattta
5701 ataagttatt tttaagtatc agttttgtga gctttaactc tatgaggtct ttgttgtttg
5761 actgtatttt aactctggcc atgacagcaa gacaaagttc catttttatt gagcttaaaa
5821 agaatcaagg ccaggtgaag tggcttacgc ctgtgatccc aacactttgt gaggctgcag
5881 caggaggatc tcttgagccc aggagtttga gaccgttcta ggcaatgtag tgaggtccag
5941 actccacaaa ataatttttt tttaaattgc acgcctgtag tctcagctat caggaggctg
6001 agatgggagg atgacttgag cccaggaaat tgaagctgca gtgaattgtg attgcaccac
6061 tgcactccag cctgggtgac agatcaagac cttgcctaaa caaaacaaaa caaacaaaac
6121 cccaaaaaac aaattgaaaa tgttgattct ttttactaca aacattatgg cagcactaaa
6181 aacttcgtgg gagtgtactg tggaaaatag tgtacttaat taattctcat tgtaatcagg
6241 ctaccaagag ccttgtgttg ctttaagagt tataactgcc aggcacagtg gctcatgcct
6301 ataatcccag caccttgaga ggccgaggca ggtggatcac ctgagatcgg gagtttgaga
6361 ccagccgggc caatatggtg aaacaagctg tgtctctact aaatacaaaa aattagccgg
6421 gcgtggtggc acatgcctgt aatcccagct gcttgggaga ctgagacagg agaattgctt
6481 gaacctggaa ggcggaggtt gcagtgagct gagattgcaa cattgtactc cagcctgggc
6541 aacaagaggg aaactccatc tcaaaaaaaa aaaaaaagtt gtaactgagg ctgggcatgg
6601 tggctcatac ctgtaatccc agcactttga aaagccgagg caggtagatc acttgagctc
6661 agaagttcga gactagcctg ggcaacatga caaaacccca tctctacaaa aaatacgaaa
6721 aattagctgg gcgtggtggc atgcacctgt agtcctagct acctgggagg ctgaggtggg
6781 aagattactt gaagctgcag tgagccatgg ttgtgccact gccctccagt ctgggcaaca
6841 aagtgagacc ctgtctcaaa aaaacaaaaa aaaattataa ctgatgtaaa ctggcagttt
6901 aggctgggtg tggtggctca agcctgtaat cctagcactt tgggaggcca aggcaggtgg
6961 atcacctgag ttcaggagtt cgagaccagc gtggccaaca tggtgaaacc ttgtctctat
7021 taaaaatacc aaaattagca agatgtggtg gtgggtgcct ataattccag ctactcagga
7081 ggctgaggca ggaggatcgc tggagccagg gaggcagagg ttacagtaag caaagatcac
7141 tccacttcac tccagcctgg gcaaaagagt gagacatatc aaaaaataaa caaataaata
7201 aataaataag tggcagttca tcatttaact ccaaagactt tgcgtacatt tctactgaaa
7261 acaatctgag ctgattagaa ccctgccatt ttatagcctt tagctcgatc tccgaccgtt
7321 catttaaaaa aattctactt caggccgggc atggtggctc aagcctgtaa tcccatcact
7381 gtaggaggcc aaagtgggca gatcacttaa ggtcaggagt ttgagaccag cctggccacc
7441 atggtgaaac cccatctcta ctaaaaatac aaaaattagc cgggcttggt ggtgagcacc
7501 tgtaatccca ccctgccgag tggcaggctg aggcaggaga atcgcttgag cccaagagcc
7561 ggaggttgca gtgagccaag cttgcaccat tgcactccag cctaggcaac agagtgtgac
```

FIG. 5D

```
7621 tccatctcaa gaaaaaaaaa attctatttc attttacaat atgcagatat atgtccatac
7681 acatgcataa tataaatgta taccatattt gtgagaatat gcatatatgt acacattaga
7741 tacacaatac aagcacaata catatgtctt ttgcccaaga tacagcattt tgtaaaggag
7801 acaggaattt agtaatatat gttccagaaa cagtacacaa gagaattcgc cgagatgaga
7861 aagttgtcac taggaatggg gagtggtaag atgtagaagg tataattgtt cttaaagttc
7921 tactgccaac tctttccaat taattaccca ctctgccatg ctttatggac aggaggttgt
7981 cggacactgt caattaataa atatttgagc atgatacact gcttggagct cctctaatat
8041 aggagagtga tatcctagtg catgttacag agggagtgtc cacacagttc ctattgtcat
8101 ttgatgagtt acttttcagg ggccttgtac ctgagcaagt tgtcctcttt ttgatggatt
8161 tcagattgag ttacctgcat tgtcttgaga ttgcagcgtg tttcctccac tgtacggcgt
8221 agtcagcaga tctattagtt aaactccagt gggccctcag tcactaaatc tatcctctgt
8281 gttgaaggct ttctgcattt gcctttcaat aaaggtttag aataactcct taaaaaa
```

SEQ ID NO. 4

FIG. 5E

NCBI Reference Sequence: NP_000782.1

```
  1 mvgslnciva vsqnmgigkn gdlpwpplrn efryfqrmtt tssvegkqnl vimgkktwfs
 61 ipeknrplkg rinlvlsrel keppqgahfl srslddalkl teqpelankv dmvwivggss
121 vykeamnhpg hlklfvtrim qdfesdtffp eidlekykll peypgvlsdv qeekgikykf
181 evyeknd
```

FIG. 6

NCBI Reference Sequence: NM_000791

```
   1 tcccagacag aacctactat gtgcggcggc agctggggcg ggaaggcggg agctgggggc
  61 gctgggggcg ctgcggccgc tgcggccgct gcagccgctg cagcgccagg gtccacctgg
 121 tcggctgcac ctgtggagga ggaggtggat ttcaggcttc ccgtagactg gaagaatcgg
 181 ctcaaaaccg cttgcctcgc aggggctgag ctggaggcag cgaggccgcc cgacgcaggc
 241 ttccggcgag acatggcagg gcaaggatgg cagcccggcg gcagggcctg gcgaggagcg
 301 cgagcccgcg gccgcagttc ccaggcgtct gcgggcgcga gcacgccgcg accctgcgtg
 361 cgccggggcg ggggggcggg gcctcgcctg cacaaatggg gacgaggggg gcggggcggc
 421 cacaatttcg cgccaaactt gaccgcgcgt tctgctgtaa cgagcgggct cggaggtcct
 481 cccgctgctg tcatggttgg ttcgctaaac tgcatcgtcg ctgtgtccca gaacatgggc
 541 atcggcaaga acggggacct gccctggcca ccgctcagga atgaattcag atatttccag
 601 agaatgacca caacctcttc agtagaaggt aaacagaatc tggtgattat gggtaagaag
 661 acctggttct ccattcctga gaagaatcga cctttaaagg gtagaattaa tttagttctc
 721 agcagagaac tcaaggaacc tccacaagga gctcattttc tttccagaag tctagatgat
 781 gccttaaaac ttactgaaca accagaatta gcaaataaag tagacatggt ctggatagtt
 841 ggtggcagtt ctgtttataa ggaagccatg aatcacccag gccatcttaa actatttgtg
 901 acaaggatca tgcaagactt tgaaagtgac acgtttttc cagaaattga tttggagaaa
 961 tataaacttc tgccagaata cccaggtgtt ctctctgatg tccaggagga gaaaggcatt
1021 aagtacaaat ttgaagtata tgagaagaat gattaatatg aaggtgtttt ctagtttaag
1081 ttgttccccc tccctctgaa aaaagtatgt atttttacat tagaaaaggt tttttgttga
1141 ctttagatct ataattattt ctaagcaact agtttttatt ccccactact cttgtctcta
1201 tcagatacca tttatgagac attcttgcta taactaagtg cttctccaag accccaactg
1261 agtccccagc acctgctaca gtgagctgcc attccacacc catcacatgt ggcactcttg
1321 ccagtccttg acattgtcgg gcttttcaca tgttggtaat atttattaaa gatgaagatc
1381 cacataccct tcaactgagc agtttcacta gtggaaatac caaaagcttc ctacgtgtat
1441 atccagaggt ttgtagataa atgttgccac cttgtttgta acagtgaaaa attgaaaaca
1501 acctggaagt ccagtgatgg gaaaatgagt atgtttctgt cttagattgg ggaacccaaa
1561 gcagattgca agactgaaat ttcagtgaaa gcagtgtatt tgctaggtca taccagaaat
1621 catcaattga ggtacggaga aactgaactg agaaggtaag aaaagcaatt taaagtcagc
1681 gagcaggttc tcattgataa caagctccat actgctgaga tacagggaaa tggagggggg
1741 aaagctggag tattgatccc gcccccctcc ttggttgtca gctccctgtc ctgtgtgtgg
1801 gcggaacata gtccagctgc tctatagcaa gtctcaggtg tttgcagtaa gaagctgctg
1861 gcatgcacgg gaacagtgaa tgccaaacac ttaaagcaat tcgatgttta agtatgtaag
1921 ttcttttttt tttagacagc gtttcgctct tgttgcccag gctagcatgc aatggtgtga
1981 cctcggctta ctgcaacctc cgccttccca gattcaagcg attctcctgc ctcaggctcc
2041 caagtagcta ggaccaggtg cgcgccacca cgcccggcta atttttgtat tttgtatttt
2101 tagtagagat ggggtttcac catgttggtc aggctagtct cgaactcgtg accgcaagcg
2161 attcacccac ctcagcctcc caaagtgctg ggattaccgg cttgagccac cacacccggc
2221 acatcttcat tctttttatg tagtaaaaag tataaggcca cacatggttt atttgaagta
2281 ttttataatt taaaaaaata cagaagcagg aaaaccaatt ataagttcaa gtgagggatg
2341 atggttgctt gaaccaaagg gttgcatgta gtaagaaatt gtgatttaag atatatttta
2401 aagttataag tagcaggata ttctgatgga gtttgacttt ggttttgggc ccagggagtt
2461 tcagatgcct ttgagaaatg aatgaagtag agagaaaata aaagaaaaac cagccaggca
2521 cagtggctca cacctgtaat cccagcgctt tgggaggcta aggcaggcag atcacttgag
2581 accagcttgg gcaacatggc aaagccccat ctctacaaaa aacacaaaaa ttagctgggc
2641 attgtggcgc acacctgtat tcccatctag tcaggaagct gagatggaag aattaattga
2701 gcccacgagt tcaaggctgc agtgagtcgt gattgtgcca ctgcactcca gccggggtga
2761 cagaagagac cttgtctcga aaaggaatct gaaaacaatg gaaccatgcc ttcataattc
2821 tagaaagtta ttttcaactg ataaatctat attcacccaa ataatcaagg gtgaaggtaa
```

FIG. 7A

```
2881 aataatacat ttttagacaa gcaaagactc aggggttacc tccatgtgcc ctttttaggg
2941 aagctgttgg agaaaatact ccagcaaaat gaaggagtac acaaaccaga gaatgacatg
3001 aatccagcaa ataggatcca acacaggcaa tattccagct atggagctag ctttaaaaag
3061 gaacagtaaa aatattaatc ggttagctgg gtggaatggc ccatgcctgt agtcccagct
3121 actcaggagg ctcagcagca ggacgacttg agcccaagag ttccagacca gcctggccac
3181 cttagtgaga tcccttctct taaaaataat aacttattgc cagatttggg gcatttggaa
3241 agaagttcat tgaagataaa gcaaaagtaa aaaaaaaaaa aaaaaaaaca aggggaaagg
3301 gttggttagg caatcattct agggcagaaa gaagtacagg ataggaagag cataatacac
3361 tgtttttctc aacaaggagc agtatgtaca cagtcataat gatgtgactg cttagcccct
3421 aaatatggta actactctgg gacaatatgg gaggaaaagt gaagattgtg atggtgtaag
3481 agctaaatcc tcatctgtca tatccagaaa tcactatata atatataata atgaaatgac
3541 taagttatgt gaggaaaaaa acagaagaca ttgctaaaag agttaaaagt cattgctctg
3601 gagaattagg agggatgggg caggggactg ttaggatgca ttataaactg aaaagccttt
3661 ttaaaatttt atgtattaat atatgcattc acttgaaaaa ctaaaaaaaa acaataattt
3721 ggaaaaaccc atgaaggtaa ctaacggaag gaaaaactaa gagaatgaaa agtatttgcc
3781 tctggaaaga acaactggca ggactgttgt tttcattgta agacttttgg agccatttaa
3841 ttgtacttaa ccattttcat ctatttcttt aataagaaca attccatctt aataaagagt
3901 tacacttgtt aataagtaaa aaaaaaaaaa aa
```

FIG. 7B

| Clone | Final Titer in Supernatant (ELISA, mg/L) |
|---|---|
| 3-324 | 66 |
| 3-388 | 48 |
| 3-261 | 287 |
| 3-330 | 268 |
| 3-503 | 215 |
| 3-351 | 170 |
| 3-269 | NA |
| 3-497 | 177 |
| 2-280 | NA |
| 3-37 | 60 |
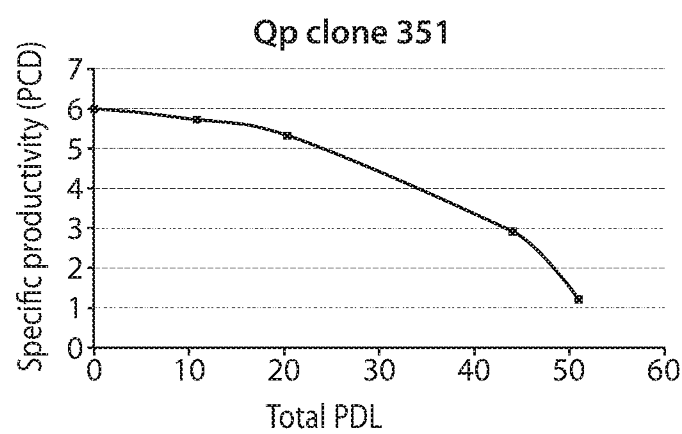
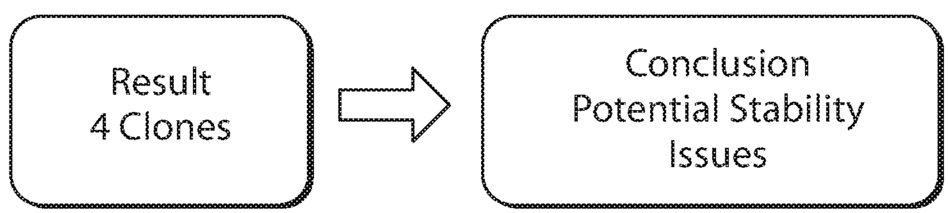
FIG. 8

METHODS OF MANUFACTURING THERAPEUTIC PROTEINS

BACKGROUND OF THE INVENTION

The production of therapeutic proteins using mammalian cell expression systems is of growing importance within the biotechnology industry. Various culture and transfection systems have been described, but each has significant limitations.

SUMMARY OF THE INVENTION

The invention described herein is based, in part, on the discovery that the combination of cholesterol-auxotrophic cells with one or more additional selection markers can be exploited in methods of manufacturing therapeutic proteins, to avoid unexpected manufacturing complications associated with cholesterol-auxotrophic cells (e.g., low productivity). In one aspect, the disclosure features methods of manufacturing a therapeutic protein, the method comprising: culturing a cholesterol-auxotrophic and glutamine-auxotrophic cell; transfecting the cell with (i) a nucleic acid encoding a protein which is capable of restoring cholesterol biosynthesis in the cell; (ii) a nucleic acid encoding a protein which is capable of restoring glutamine biosynthesis in the cell; and (iii) a nucleic acid encoding the therapeutic protein; culturing the cell under conditions suitable for expression of the therapeutic protein; and isolating and/or purifying the therapeutic protein.

In one embodiment, the cell is an NS0 cell.

In some embodiments, the therapeutic protein is an antibody. In some embodiments, the therapeutic protein is a fusion protein. In some embodiments, the therapeutic protein is an Fc-containing fusion protein.

In some embodiments, in the transfecting step the cell is transfected with nucleic acids (iii) encoding an antibody light chain and an antibody heavy chain. In some embodiments, nucleic acid (i) encodes a 3-ketosteroid reductase. In some embodiments, the nucleic acid (ii) encodes a glutamine synthetase.

In some embodiments, a first expression vector comprises nucleic acid (i) and (iii), and a second expression vector comprises nucleic acids (ii). In some embodiments, a first expression vector comprises nucleic acid (i), and a second expression vector comprises nucleic acids (ii) and (iii). In some embodiments, transfection of the first expression vector is performed prior to transfection of the second expression vector. In some embodiments, transfection of the first expression vector is performed simultaneously with transfection of the second expression vector.

In some embodiments, the cell is cultured (e.g., after transfection of nucleic acid (i)) in the absence of exogenously introduced cholesterol. In some embodiments, the cell is cultured (e.g., after transfection of nucleic acid (ii)) in the absence of exogenously introduced glutamine. In some embodiments, the cell is cultured (e.g., during and/or after transfection of nucleic acid (ii)) in the presence of a glutamine synthetase inhibitor (e.g., methionine sulfoximine). In some embodiments, the cell is cultured (e.g., during and/or after transfection of nucleic acid (i)) in the presence of a 3-ketosteriod reductase inhibitor.

In some embodiments, the cell is cultured in absence of exogenously introduced cholesterol and in the absence of exogenously introduced glutamine. In some embodiments, the cell is cultured in absence of exogenously introduced cholesterol, in the absence of exogenously introduced glutamine, and in the presence of a glutamine synthetase inhibitor (e.g., methionine sulfoximine). In some embodiments, the cell is cultured (e.g., after transfection of nucleic acid (i)) in the absence of exogenously introduced cholesterol and the cell is cultured (e.g., after transfection of nucleic acid (ii)) in the absence of exogenously introduced glutamine.

In one aspect, the disclosure features methods of manufacturing a therapeutic protein, the method comprising: culturing a cholesterol-auxotrophic cell; transfecting the cell with (i) a nucleic acid encoding a protein which is capable of restoring cholesterol biosynthesis in the cell; (ii) a nucleic acid encoding a protein expressing one or more selectable marker; and (iii) a nucleic acid encoding the therapeutic protein; culturing the cell under conditions suitable for expression of the therapeutic protein; and isolating and/or purifying the therapeutic protein.

In one embodiment, the cell is an NS0 cell.

In some embodiments, the therapeutic protein is an antibody. In some embodiments, the therapeutic protein is a fusion protein. In some embodiments, the therapeutic protein is an Fc-containing fusion protein.

In some embodiments, in the transfecting step the cell is transfected with nucleic acids (iii) encoding an antibody light chain and an antibody heavy chain.

In some embodiments, nucleic acid (i) encodes a 3-ketosteroid reductase.

In some embodiments, the nucleic acid (ii) encodes a glutamine synthetase, a dihydrofolate reductase (DHFR), or one or more antibiotic resistance gene (e.g., neomycin, blasticidin, hygromyocin, puromycin, zeocin, mycophenolic acid).

In some embodiments, a first expression vector comprises nucleic acid (i) and (iii), and a second expression vector comprises nucleic acids (ii). In some embodiments, a first expression vector comprises nucleic acid (i), and a second expression vector comprises nucleic acids (ii) and (iii). In some embodiments, transfection of the first expression vector is performed prior to transfection of the second expression vector. In some embodiments, transfection of the first expression vector is performed simultaneously with transfection of the second expression vector.

In some embodiments, the cell is cultured (e.g., after transfection of nucleic acid (i)) in the absence of exogenously introduced cholesterol. In some embodiments, the cell is cultured (e.g., during and/or after transfection of nucleic acid (i)) in the presence of a 3-ketosteriod reductase inhibitor. In some embodiments, the cell is cultured in absence of exogenously introduced cholesterol.

In one aspect, the disclosure features methods of manufacturing a therapeutic protein, the method comprising: culturing a cholesterol-auxotrophic cell that does not express a functional dihydrofolate reductase (DHFR); transfecting the cell with (i) a nucleic acid encoding a protein which is capable of restoring cholesterol biosynthesis in the cell; (ii) a nucleic acid encoding a DHFR; and (iii) a nucleic acid encoding the therapeutic protein; culturing the cell under conditions suitable for expression of the therapeutic protein; and isolating and/or purifying the therapeutic protein.

In one embodiment, the cell is an NS0 cell.

In some embodiments, the therapeutic protein is an antibody. In some embodiments, the therapeutic protein is a fusion protein. In some embodiments, the therapeutic protein is an Fc-containing fusion protein.

In some embodiments, in the transfecting step the cell is transfected with nucleic acids (iii) encoding an antibody light chain and an antibody heavy chain. In some embodiments, nucleic acid (i) encodes a 3-ketosteroid reductase.

In some embodiments, a first expression vector comprises nucleic acid (i) and (iii), and a second expression vector comprises nucleic acids (ii). In some embodiments, a first expression vector comprises nucleic acid (i), and a second expression vector comprises nucleic acids (ii) and (iii). In some embodiments, transfection of the first expression vector is performed prior to transfection of the second expression vector. In some embodiments, transfection of the first expression vector is performed simultaneously with transfection of the second expression vector.

In some embodiments, the cell is cultured (e.g., after transfection of nucleic acid (i)) in the absence of exogenously introduced cholesterol. In some embodiments, the cell is cultured (e.g., during and/or after transfection of nucleic acid (ii)) in the presence of a DHFR inhibitor (e.g., methionine sulphoximine (MSX)). In some embodiments, the cell is cultured (e.g., during and/or after transfection of nucleic acid (i)) in the presence of a 3-ketosteriod reductase inhibitor.

In some embodiments, the cell is cultured in absence of exogenously introduced cholesterol. In some embodiments, the cell is cultured in absence of exogenously introduced cholesterol and in the presence of a DHFR inhibitor (e.g., methionine sulphoximine (MSX)).

In one aspect, the disclosure features methods of manufacturing a therapeutic protein, the method comprising: culturing a cholesterol-auxotrophic cell that is sensitive to neomycin; transfecting the cell with (i) a nucleic acid encoding a protein which is capable of restoring cholesterol biosynthesis in the cell; (ii) a nucleic acid encoding a neomycin resistance gene; and (iii) a nucleic acid encoding the therapeutic protein; culturing the cell under conditions suitable for expression of the therapeutic protein; and isolating and/or purifying the therapeutic protein.

In one embodiment, the cell is an NS0 cell.

In some embodiments, the therapeutic protein is an antibody. In some embodiments, the therapeutic protein is a fusion protein. In some embodiments, the therapeutic protein is an Fc-containing fusion protein.

In some embodiments, in the transfecting step the cell is transfected with nucleic acids (iii) encoding an antibody light chain and an antibody heavy chain. In some embodiments, nucleic acid (i) encodes a 3-ketosteroid reductase. In some embodiments, the nucleic acid (ii) encodes the neomycin resistance gene from Tn5 encoding an aminoglycoside 3'-phosphotransferase (APH 3' II).

In some embodiments, a first expression vector comprises nucleic acid (i) and (iii), and a second expression vector comprises nucleic acids (ii). In some embodiments, a first expression vector comprises nucleic acid (i), and a second expression vector comprises nucleic acids (ii) and (iii). In some embodiments, transfection of the first expression vector is performed prior to transfection of the second expression vector. In some embodiments, transfection of the first expression vector is performed simultaneously with transfection of the second expression vector.

In some embodiments, both the first and second expression vector contains HC and LC one vector contains KSR and the other vector contains GS or another antibiotic resistant gene. In some embodiments, there are three separate vectors (e.g., for triple selection), wherein all three vectors contains HC and LC; a first vector contains KSR, a second vector contains GS, and a third vector contains any antibiotic resistant gene, e.g. NEO.

In some embodiments, the cell is cultured (e.g., after transfection of nucleic acid (i)) in the absence of exogenously introduced cholesterol. In some embodiments, the cell is cultured (e.g., during and/or after transfection of nucleic acid (ii)) in the presence of an aminoglycoside antibiotic (e.g., G418). In some embodiments, the cell is cultured (e.g., during and/or after transfection of nucleic acid (i)) in the presence of a 3-ketosteriod reductase inhibitor.

In some embodiments, the cell is cultured in absence of exogenously introduced cholesterol. In some embodiments, the cell is cultured in absence of exogenously introduced cholesterol and in the presence of an aminoglycoside antibiotic (e.g., G418).

In one aspect, the disclosure features methods of manufacturing a therapeutic protein, the method comprising: culturing a cholesterol-auxotrophic cell that is sensitive to blasticidin; transfecting the cell with (i) a nucleic acid encoding a protein which is capable of restoring cholesterol biosynthesis in the cell; (ii) a nucleic acid encoding a blasticidin resistance gene; and (iii) a nucleic acid encoding the therapeutic protein; culturing the cell under conditions suitable for expression of the therapeutic protein; and isolating and/or purifying the therapeutic protein.

In one embodiment, the cell is an NS0 cell.

In some embodiments, the therapeutic protein is an antibody. In some embodiments, the therapeutic protein is a fusion protein. In some embodiments, the therapeutic protein is an Fc-containing fusion protein.

In some embodiments, in the transfecting step the cell is transfected with nucleic acids (iii) encoding an antibody light chain and an antibody heavy chain. In some embodiments, nucleic acid (i) encodes a 3-ketosteroid reductase. In some embodiments, the nucleic acid (ii) encodes the blasticidin resistance gene from *Bacillus cereus* (which codes for blasticidin-S deaminase).

In some embodiments, a first expression vector comprises nucleic acid (i) and (iii), and a second expression vector comprises nucleic acids (ii). In some embodiments, a first expression vector comprises nucleic acid (i), and a second expression vector comprises nucleic acids (ii) and (iii). In some embodiments, transfection of the first expression vector is performed prior to transfection of the second expression vector. In some embodiments, transfection of the first expression vector is performed simultaneously with transfection of the second expression vector.

In some embodiments, the cell is cultured (e.g., after transfection of nucleic acid (i)) in the absence of exogenously introduced cholesterol. In some embodiments, the cell is cultured (e.g., during and/or after transfection of nucleic acid (ii)) in the presence of a peptidyl nucleoside antibiotic (e.g., blasticidin). In some embodiments, the cell is cultured (e.g., during and/or after transfection of nucleic acid (i)) in the presence of a 3-ketosteriod reductase inhibitor.

In some embodiments, the cell is cultured in absence of exogenously introduced cholesterol. In some embodiments, the cell is cultured in absence of exogenously introduced cholesterol and in the presence of a peptidyl nucleoside antibiotic an aminoglycoside antibiotic (e.g., blasticidin).

In one aspect, the disclosure features methods of manufacturing a therapeutic protein, the method comprising: culturing a cholesterol-auxotrophic cell that is sensitive to hygromycin B; transfecting the cell with (i) a nucleic acid encoding a protein which is capable of restoring cholesterol biosynthesis in the cell; (ii) a nucleic acid encoding a hygromycin B resistance gene; and (iii) a nucleic acid encoding the therapeutic protein; culturing the cell under conditions suitable for expression of the therapeutic protein; and isolating and/or purifying the therapeutic protein.

In one embodiment, the cell is an NS0 cell.

In some embodiments, the therapeutic protein is an antibody. In some embodiments, the therapeutic protein is a fusion protein. In some embodiments, the therapeutic protein is an Fc-containing fusion protein.

In some embodiments, in the transfecting step the cell is transfected with nucleic acids (iii) encoding an antibody light chain and an antibody heavy chain. In some embodiments, nucleic acid (i) encodes a 3-ketosteroid reductase. In some embodiments, the nucleic acid (ii) encodes a hygromycin B phosphotransferase.

In some embodiments, a first expression vector comprises nucleic acid (i) and (iii), and a second expression vector comprises nucleic acids (ii). In some embodiments, a first expression vector comprises nucleic acid (i), and a second expression vector comprises nucleic acids (ii) and (iii). In some embodiments, transfection of the first expression vector is performed prior to transfection of the second expression vector. In some embodiments, transfection of the first expression vector is performed simultaneously with transfection of the second expression vector.

In some embodiments, the cell is cultured (e.g., after transfection of nucleic acid (i)) in the absence of exogenously introduced cholesterol. In some embodiments, the cell is cultured (e.g., during and/or after transfection of nucleic acid (ii)) in the presence of an aminoglycoside antibiotic (e.g., hygromycin B). In some embodiments, the cell is cultured (e.g., during and/or after transfection of nucleic acid (i)) in the presence of a 3-ketosteriod reductase inhibitor.

In some embodiments, the cell is cultured in absence of exogenously introduced cholesterol. In some embodiments, the cell is cultured in absence of exogenously introduced cholesterol and in the presence of a peptidyl nucleoside antibiotic an aminoglycoside antibiotic (e.g., hygromycin B).

In one aspect, the disclosure features methods of manufacturing a therapeutic protein, the method comprising: culturing a cholesterol-auxotrophic cell that is sensitive to puromycin; transfecting the cell with (i) a nucleic acid encoding a protein which is capable of restoring cholesterol biosynthesis in the cell; (ii) a nucleic acid encoding a puromycin resistance gene; and (iii) a nucleic acid encoding the therapeutic protein; culturing the cell under conditions suitable for expression of the therapeutic protein; and isolating and/or purifying the therapeutic protein.

In one embodiment, the cell is an NS0 cell.

In some embodiments, the therapeutic protein is an antibody. In some embodiments, the therapeutic protein is a fusion protein. In some embodiments, the therapeutic protein is an Fc-containing fusion protein.

In some embodiments, in the transfecting step the cell is transfected with nucleic acids (iii) encoding an antibody light chain and an antibody heavy chain. In some embodiments, nucleic acid (i) encodes a 3-ketosteroid reductase. In some embodiments, the nucleic acid (ii) encodes a puromycin N-acetyl-transferase.

In some embodiments, a first expression vector comprises nucleic acid (i) and (iii), and a second expression vector comprises nucleic acids (ii). In some embodiments, a first expression vector comprises nucleic acid (i), and a second expression vector comprises nucleic acids (ii) and (iii). In some embodiments, transfection of the first expression vector is performed prior to transfection of the second expression vector. In some embodiments, transfection of the first expression vector is performed simultaneously with transfection of the second expression vector.

In some embodiments, the cell is cultured (e.g., after transfection of nucleic acid (i)) in the absence of exogenously introduced cholesterol. In some embodiments, the cell is cultured (e.g., during and/or after transfection of nucleic acid (ii)) in the presence of an aminonucleoside antibiotic (e.g., puromycin). In some embodiments, the cell is cultured (e.g., during and/or after transfection of nucleic acid (i)) in the presence of a 3-ketosteriod reductase inhibitor.

In some embodiments, the cell is cultured in absence of exogenously introduced cholesterol. In some embodiments, the cell is cultured in absence of exogenously introduced cholesterol and in the presence of a peptidyl nucleoside antibiotic an aminonucleoside antibiotic (e.g., puromycin).

In one aspect, the disclosure features methods of manufacturing a therapeutic protein, the method comprising: culturing a cholesterol-auxotrophic cell that is sensitive to zeocin; transfecting the cell with (i) a nucleic acid encoding a protein which is capable of restoring cholesterol biosynthesis in the cell; (ii) a nucleic acid encoding a zeocin resistance gene; and (iii) a nucleic acid encoding the therapeutic protein; culturing the cell under conditions suitable for expression of the therapeutic protein; and isolating and/or purifying the therapeutic protein.

In one embodiment, the cell is an NS0 cell.

In some embodiments, the therapeutic protein is an antibody. In some embodiments, the therapeutic protein is a fusion protein. In some embodiments, the therapeutic protein is an Fc-containing fusion protein.

In some embodiments, in the transfecting step the cell is transfected with nucleic acids (iii) encoding an antibody light chain and an antibody heavy chain. In some embodiments, nucleic acid (i) encodes a 3-ketosteroid reductase. In some embodiments, the nucleic acid (ii) encodes a Sh ble gene product.

In some embodiments, a first expression vector comprises nucleic acid (i) and (iii), and a second expression vector comprises nucleic acids (ii). In some embodiments, a first expression vector comprises nucleic acid (i), and a second expression vector comprises nucleic acids (ii) and (iii). In some embodiments, transfection of the first expression vector is performed prior to transfection of the second expression vector. In some embodiments, transfection of the first expression vector is performed simultaneously with transfection of the second expression vector.

In some embodiments, the cell is cultured (e.g., after transfection of nucleic acid (i)) in the absence of exogenously introduced cholesterol. In some embodiments, the cell is cultured (e.g., during and/or after transfection of nucleic acid (ii)) in the presence of a copper-chelated glycopeptide antibiotic (e.g., zeocin). In some embodiments, the cell is cultured (e.g., during and/or after transfection of nucleic acid (i)) in the presence of a 3-ketosteriod reductase inhibitor. In some embodiments, the cell is cultured in absence of exogenously introduced cholesterol. In some embodiments, the cell is cultured in absence of exogenously introduced cholesterol and in the presence of a copper-chelated glycopeptide antibiotic (e.g., zeocin).

In one aspect, the disclosure features methods of manufacturing a therapeutic protein, the method comprising: culturing a cholesterol-auxotrophic cell that is sensitive to mycophenolic Acid (MPA); transfecting the cell with (i) a nucleic acid encoding a protein which is capable of restoring cholesterol biosynthesis in the cell; (ii) a nucleic acid encoding a MPA resistance gene; and (iii) a nucleic acid encoding the therapeutic protein; culturing the cell under conditions suitable for expression of the therapeutic protein; and isolating and/or purifying the therapeutic protein.

In one embodiment, the cell is an NS0 cell.

In some embodiments, the therapeutic protein is an antibody. In some embodiments, the therapeutic protein is a fusion protein. In some embodiments, the therapeutic protein is an Fc-containing fusion protein.

In some embodiments, in the transfecting step the cell is transfected with nucleic acids (iii) encoding an antibody light chain and an antibody heavy chain. In some embodiments, nucleic acid (i) encodes a 3-ketosteroid reductase. In some embodiments, the nucleic acid (ii) encodes the xanthine-guanine phosphoribosyltransferase (Ecogpt) gene.

In some embodiments, a first expression vector comprises nucleic acid (i) and (iii), and a second expression vector comprises nucleic acids (ii). In some embodiments, a first expression vector comprises nucleic acid (i), and a second expression vector comprises nucleic acids (ii) and (iii). In some embodiments, transfection of the first expression vector is performed prior to transfection of the second expression vector. In some embodiments, transfection of the first expression vector is performed simultaneously with transfection of the second expression vector.

In some embodiments, the cell is cultured (e.g., after transfection of nucleic acid (i)) in the absence of exogenously introduced cholesterol. In some embodiments, the cell is cultured (e.g., during and/or after transfection of nucleic acid (ii)) in the presence of MPA. In some embodiments, the cell is cultured (e.g., during and/or after transfection of nucleic acid (i)) in the presence of a 3-ketosteriod reductase inhibitor.

In some embodiments, the cell is cultured in absence of exogenously introduced cholesterol. In some embodiments, the cell is cultured in absence of exogenously introduced cholesterol and in the presence of MPA.

In one aspect, the disclosure features methods of manufacturing a therapeutic protein, the method comprising: culturing a cholesterol-auxotrophic cell that is sensitive to mycophenolic acid (MPA); transfecting the cell with (i) a nucleic acid encoding a protein which is capable of restoring cholesterol biosynthesis in the cell; (ii) a nucleic acid encoding a MPA resistance gene; and (iii) a nucleic acid encoding the therapeutic protein; culturing the cell under conditions suitable for expression of the therapeutic protein; and isolating and/or purifying the therapeutic protein.

In one embodiment, the cell is an NS0 cell.

In some embodiments, the therapeutic protein is an antibody. In some embodiments, the therapeutic protein is a fusion protein. In some embodiments, the therapeutic protein is an Fc-containing fusion protein.

In some embodiments, in the transfecting step the cell is transfected with nucleic acids (iii) encoding an antibody light chain and an antibody heavy chain. In some embodiments, nucleic acid (i) encodes a 3-ketosteroid reductase. In some embodiments, the nucleic acid (ii) encodes the xanthine-guanine phosphoribosyltransferase (Ecogpt) gene.

In some embodiments, a first expression vector comprises nucleic acid (i) and (iii), and a second expression vector comprises nucleic acids (ii). In some embodiments, a first expression vector comprises nucleic acid (i), and a second expression vector comprises nucleic acids (ii) and (iii). In some embodiments, transfection of the first expression vector is performed prior to transfection of the second expression vector. In some embodiments, transfection of the first expression vector is performed simultaneously with transfection of the second expression vector.

In some embodiments, the cell is cultured (e.g., after transfection of nucleic acid (i)) in the absence of exogenously introduced cholesterol. In some embodiments, the cell is cultured (e.g., during and/or after transfection of nucleic acid (ii)) in the presence of MPA. In some embodiments, the cell is cultured (e.g., during and/or after transfection of nucleic acid (i)) in the presence of a 3-ketosteriod reductase inhibitor.

In some embodiments, the cell is cultured in absence of exogenously introduced cholesterol. In some embodiments, the cell is cultured in absence of exogenously introduced cholesterol and in the presence of MPA.

In one aspect, the disclosure features methods of manufacturing a therapeutic protein, the method comprising: culturing a cholesterol-auxotrophic and glutamine-auxotrophic cell; transfecting the cell with (i) a nucleic acid encoding a protein which is capable of restoring cholesterol biosynthesis in the cell (e.g., KSR); (ii) a nucleic acid encoding a protein which is capable of restoring glutamine biosynthesis in the cell (e.g., glutathione synthetase); (iii) a nucleic acid encoding a protein which is capable of providing resistance to G418 (e.g., neomycin resistance gene); and (iv) a nucleic acid encoding the therapeutic protein (e.g., an antibody, e.g., a heavy chain and light chain); culturing the cell under conditions suitable for expression of the therapeutic protein; and isolating and/or purifying the therapeutic protein.

In some embodiments, nucleic acid (iii) is transfected first and during and/post transfection G418 is added to the cell culture media. In some embodiments, nucleic acid (iii) is transfected first and during and/or post transfection G418 is added to the cell culture media; and nucleic acid (ii) is transfected second and during and/or post transfection cholesterol is absent from the cell culture media. In some embodiments, nucleic acid (iii) is transfected first and during and/or post transfection G418 is added to the cell culture media; and nucleic acid (ii) is transfected second and during and/or post transfection cholesterol is absent from the cell culture media (e.g., exogenously added cholesterol); and nucleic acid (i) is transfected third and during/post transfection glutamine is absent from the cell culture medium (e.g., exogenously added glutamine) (optionally methionine sulphoximine (MSX) is added to the cell culture media).

In some embodiments, nucleic acid (ii) and (i) are transfected simultaneously, wherein G418 is added to the cell culture media and the cell culture media does not contain cholesterol (e.g., exogenously added cholesterol). In some embodiments, nucleic acids (i), (ii), (iii), and (iv) are transfected simultaneously, wherein the G418 is added to the cell culture media and the cell culture media does not contain cholesterol (e.g., exogenously added cholesterol) and does not contain glutamine (e.g., exogenously added glutamine) (optionally methionine sulphoximine (MSX) is added to the cell culture media). In some embodiments, nucleic acid (iv) is incorporated in the same nucleic acid sequence (e.g., vector) as each of (i), (ii), and (iii). In some embodiments, nucleic acid (iv) is incorporated in the same nucleic acid sequence (e.g., vector) as each of (i) and (ii); (i) and (iii); or (ii) and (iii). In some embodiments, nucleic acid (iv) encodes the heavy and light chain of a therapeutic antibody. In some embodiments, the light chain is incorporated in the same nucleic acid sequence (e.g., vector) as each of (i) and (ii); (i) and (iii); (ii) and (iii); or (i), (ii), and (iii). In some embodiments, the heavy chain is incorporated in the same nucleic acid sequence (e.g., vector) as each of (i) and (ii); (i) and (iii); (ii) and (iii); or (i), (ii), and (iii). In some embodiments, the light chain and heavy chain is incorporated in the same nucleic acid sequence (e.g., vector) as each of (i) and (ii); (i) and (iii); (ii) and (iii); or (i), (ii), and (iii).

In some embodiments, any of nucleic acids (i), (ii), (iii), and (iv) are incorporated into a single nucleic acid (e.g., single vector). For example, in some embodiments, nucleic acids (i) and (ii); (i) and (iii); (i) and (iv); (i), (ii), and (iii); (i), (ii), (iii), and (iv); (ii) and (iii); or (ii) and (iv); (iii) and (iv); are incorporated on a single nucleic acid. In some embodiments, nucleic acid (iv) comprises two separate nucleic acids, one encoding a heavy chain and one encoding a light chain of a therapeutic antibody. In some embodiments the heavy chain is incorporated onto another nucleic acid, e.g., (i), (ii), or (iii). In some embodiments the light chain is incorporated onto another nucleic acid, e.g., (i), (ii), or (iii).

In one embodiment, the cell is an NS0 cell.

In some embodiments, the therapeutic protein is an antibody. In some embodiments, the therapeutic protein is a fusion protein. In some embodiments, the therapeutic protein is an Fc-containing fusion protein.

In some embodiments, in the transfecting step the cell is transfected with nucleic acids (iv) encoding an antibody light chain and an antibody heavy chain. In some embodiments, nucleic acid (i) encodes a 3-ketosteroid reductase. In some embodiments, the nucleic acid (ii) encodes a glutamine synthetase. In some embodiments, the nucleic acid (iii) encodes neomycin resistance gene.

In some embodiments, a first expression vector comprises nucleic acid (i) and (iv), and a second expression vector comprises nucleic acids (ii). In some embodiments, a first expression vector comprises nucleic acid (i), and a second expression vector comprises nucleic acids (ii) and (iv). In some embodiments, transfection of the first expression vector is performed prior to transfection of the second expression vector. In some embodiments, transfection of the first expression vector is performed simultaneously with transfection of the second expression vector.

In some embodiments, the cell is cultured (e.g., after transfection of nucleic acid (i)) in the absence of exogenously introduced cholesterol. In some embodiments, the cell is cultured (e.g., after transfection of nucleic acid (ii)) in the absence of exogenously introduced glutamine. In some embodiments, the cell is cultured (e.g., during and/or after transfection of nucleic acid (ii)) in the presence of a glutamine synthetase inhibitor (e.g., methionine sulfoximine). In some embodiments, the cell is cultured (e.g., during and/or after transfection of nucleic acid (i)) in the presence of a 3-ketosteriod reductase inhibitor.

In some embodiments, the cell is cultured in absence of exogenously introduced cholesterol and in the absence of exogenously introduced glutamine. In some embodiments, the cell is cultured in absence of exogenously introduced cholesterol, in the absence of exogenously introduced glutamine, and in the presence of a glutamine synthetase inhibitor (e.g., methionine sulfoximine). In some embodiments, the cell is cultured (e.g., after transfection of nucleic acid (i)) in the absence of exogenously introduced cholesterol and the cell is cultured (e.g., after transfection of nucleic acid (ii)) in the absence of exogenously introduced glutamine.

BRIEF DESCRIPTION OF THE FIGURES

FIG. 2 depicts the NCBI reference amino acid sequence of 3-ketosteroid reductase (NP_057455) (SEQ ID No. 1).

FIG. 3 depicts the NCBI reference mRNA sequence of HSD17β7 (NM_016371.3) (SEQ ID No. 2).

FIG. 4 depicts the NCBI reference amino acid sequence of glutamine synthetase (NP_002056.2) (SEQ ID No. 3).

FIG. 5A-E depicts the NCBI reference mRNA sequence of glutamine synthetase (NM_002065.6) (SEQ ID No. 4).

FIG. 6 depicts the NCBI reference amino acid sequence of dihydrofolate reductase (DHFR) (NP_000782.1) (SEQ ID No. 5).

FIG. 7A-B depicts the NCBI reference mRNA sequence of DHFR (NM_000791.3) (SEQ ID No. 6).

FIG. 8 depicts the stability of proteins produced using the 3-KSR cell culture system. FIG. 8 lists the final protein titer in the supernatant of 3-KSR cells for 10 different 3-KSR cell clones. Four clones (3-261, 3-330, 3-351, 3-497) demonstrated high protein titer. However, as further shown in FIG. 8 3-KSR clone 3-351, demonstrated a decline in cell specific productivity.

DETAILED DESCRIPTION OF THE INVENTION

Figure 1:
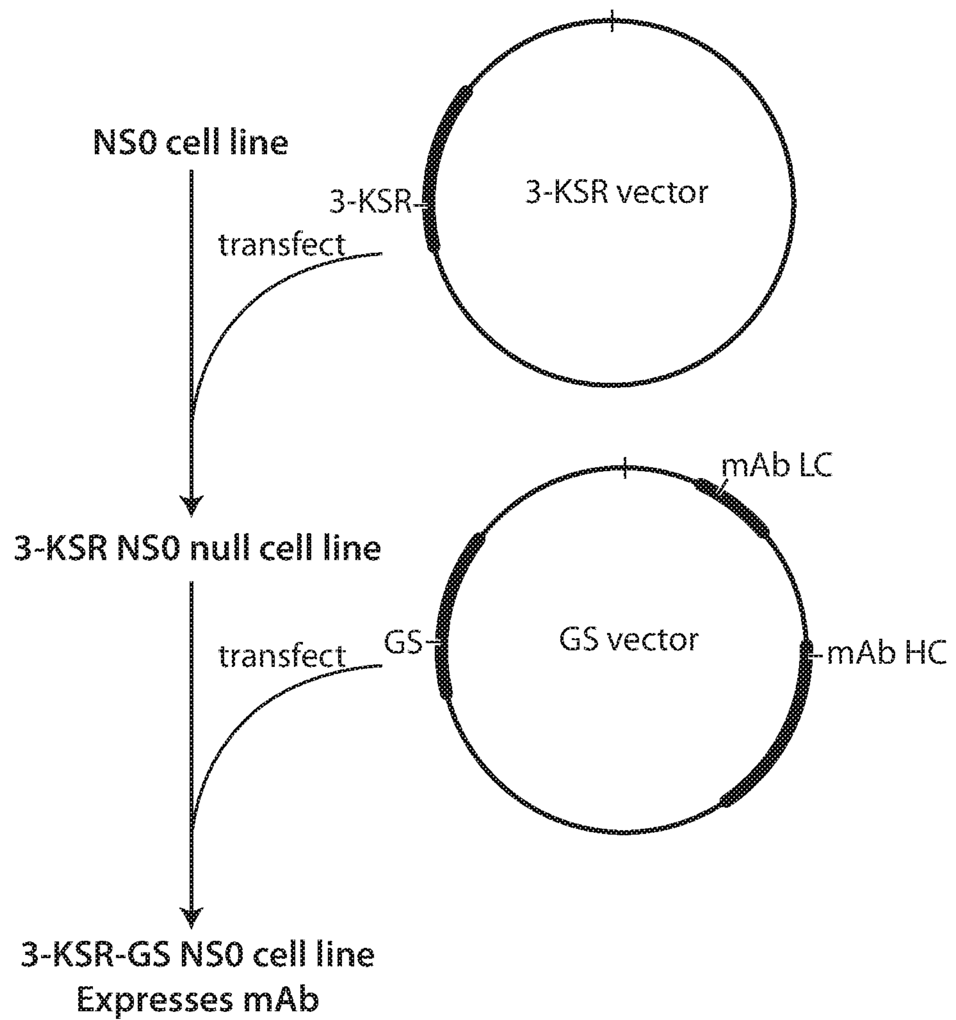
FIG. 1 depicts an exemplary protocol of the methods described herein.

In certain recombinant protein production systems, such as NS0 host cell systems, cholesterol-auxotrophy is exploited by incorporating a 3-ketosteroid reductase (3-KSR) gene into the vector encoding the therapeutic protein, and recombinant cells selected for by removing cholesterol from the culture media (US20100028940). However, the inventors of the present disclosure unexpectedly found that this system can suffer from low productivity (e.g., protein product per cell per day) and low protein titers due to the difficulty of amplification in this cell line (see e.g., FIG. 8). In other NS0 host cell systems, glutamine-auxotrophy is exploited by incorporating a glutamine synthetase (GS) gene into the vector encoding the therapeutic protein, and transfected cells are selected for by removing glutamine from the culture media. In addition, a GS inhibitor can be added to the culture media to drive selection towards the incorporation multiple copies of the GS gene and therefore the gene encoding the protein of interest (Barnes et al. Cytotechnology. 2000. *Advances in animal cell recombinant protein production: GS-NS0 expression system* February; 32(2):109-23). Each system has different limitations. Described herein are alternate methods of manufacturing therapeutic products in, e.g., an NS0 host cell system.

A "glutamine-auxotrophic" cell as used herein is defined as a cell which does not synthesize any glutamine or does not synthesize enough glutamine to be capable of survival and growth in glutamine-free cell culture medium.

A "cholesterol-auxotrophic" cell as used herein is defined as a cell which does not synthesize any cholesterol or does not synthesize enough cholesterol to be capable of survival and growth in cholesterol-free cell culture medium.

"Restoring glutamine biosynthesis" as used herein means increasing the level of glutamine biosynthesis in a cell (from the level in a glutamine-auxotrophic cell), to at least a level which enables the cell to survive and grow in glutamine-free cell culture medium.

"Restoring cholesterol biosynthesis" as used herein means increasing the level of cholesterol biosynthesis in a cell (from the level in a cholesterol-auxotrophic cell), to at least a level which enables the cell to survive and grow in cholesterol-free cell culture medium.

"Survive and grow" or "survival and growth" as used herein refers to the ability of a cell or culture of cells to maintain greater than 60% cell viability during log phase growth as measured by trypan blue exclusion.

3-Ketosteroid Reductase (KSR)

The enzyme 3-ketosteroid reductase is encoded by the HSD17β7 gene, and functions as a 3-ketosteroid reductase in the biosynthesis of cholesterol (Marijanovic et al., Mol Endocrinol. 2003 September; 17(9):1715-25). See FIG. 2 (SEQ ID No.1) and FIG. 3 (SEQ ID No.2) respectively, for NCBI reference amino acid (NP_057455) and mRNA sequence (NM_016371.3).

Glutamine Synthetase (GS)

The enzyme glutamine synthetase encoded by the glutamine synthetase gene catalyzes the synthesis of glutamine from glutamate and ammonia (Eisenberg et al., Biochimica et Biophysica Acta, 2000, Vol 1477, 122-145). Several alternatively spliced transcript variants have been found for this gene. See FIG. 4 (SEQ ID No.3) and FIG. 5 (SEQ ID No.4) respectively, for NCBI reference amino acid NP_002056.2 and mRNA sequence NM_002065.6.

Dihydrofolate Reductase (DHFR)

The enzyme DHFR is encoded by the DHFR gene, and converts dihydrofolate into tetrahydrofolate, a methyl group shuttle required for the de novo synthesis of purines, thymidylic acid, and certain amino acids. Several alternatively spliced transcript variants have been found for this gene. See FIG. 6 (SEQ ID No.5) and FIG. 7 (SEQ ID No.6) respectively, for NCBI reference amino acid (NP_000782.1) and mRNA sequence (NM_000791.3).

Antibiotic Resistance Gene Selection Markers

Antibiotic resistance genes are commonly used positive selection markers used in mammalian cell culture (see e.g., Antibody Expression and Production, Editor Mohamed Al-Rubeai, Springer Netherlands, Springer Science Business Media B.V., ISBN 978-94-007-1256-0; Cell Line Development, Mohamed Al-Rubeai Aug. 11, 2009 Springer Science & Business Media). Exemplary antibiotic resistance genes include but are not limited to genes conferring resistance to neomycin resistance gene, blasticidin, hygromyocin, puromycin, zeocin, mycophenolic acid. Suitable antibiotic resistance genes and corresponding inhibitors for use in cell selection would be known to one of skill in the art.

TABLE 1

Exemplary Antibiotic Selection Markers

| Antibiotic | Mechanism of Action | Resistance Gene |
|---|---|---|
| Hygromycin B | Hygromycin B is an aminoglycoside antibiotic produced by Streptomyces hygroscopicus. Hygromycin B inhibits protein synthesis. It has been reported to interfere with translocation and to cause mistranslation at the 70S ribosome. | The hph gene. |
| Zeocin ® | Zeocin ® is a copper-chelated glycopeptide antibiotic produced by Streptomyces CL990. Zeocin ™ causes cell death by intercalating into DNA and cleaving it. | The Sh ble gene. |
| Blasticidin | Blasticidin is a peptidyl nucleoside antibiotic isolated from Streptomyces griseochromogenes that inhibits protein synthesis by interfering with the peptide-bond formation in the ribosomal machinery. | The blasticidin resistance gene from Bacillus cereus (bsr), which codes for blasticidin-S deaminase. |
| Puromycin | Puromycin is an aminonucleoside antibiotic produced by Streptomyces alboniger. It specifically inhibits peptidyl transfer on both prokaryotic and eukaryotic ribosomes. | The Pac gene encoding a puromycin N-acetyl-transferase (PAC) that was found in a Streptomyces producer strain. |
| Geneticin | G418 (Geneticin) is an aminoglycoside antibiotic similar in structure to gentamicin B1, produced by Micromonospora rhodorangea. G418 blocks polypeptide synthesis by inhibiting the elongation step in both prokaryotic and eukaryotic cells. | The Neomycin resistance gene (neo) from Tn5 encoding an aminoglycoside 3'-phosphotransferase, APH 3' II. |

TABLE 1-continued

| Exemplary Antibiotic Selection Markers | | |
|---|---|---|
| Antibiotic | Mechanism of Action | Resistance Gene |
| Phleomycin | Phleomycin is a glycopeptide antibiotic of the bleomycin family, isolated from a mutant strain of Streptomyces verticillus. It binds and intercalates DNA thus destroying the integrity of the double helix. | The Sh ble gene from Streptoalloteichus hindustanus which encodes a protein that binds to phleomycin, inhibiting its DNA cleavage activity. |

Vectors, Host Cells, and Therapeutic Protein Production

The therapeutic proteins of the invention can be produced from a host cell. A host cell refers to a vehicle that includes the necessary cellular components, e.g., organelles, needed to express the polypeptides and constructs described herein from their corresponding nucleic acids. The nucleic acids may be included in nucleic acid vectors that can be introduced into the host cell by conventional techniques known in the art (e.g., transformation, transfection, electroporation, calcium phosphate precipitation, direct microinjection, infection, etc). The choice of nucleic acid vectors depends in part on the host cells to be used. Generally, preferred host cells are of either prokaryotic (e.g., bacterial) or eukaryotic (e.g., mammalian) origin.

Nucleic Acid Vector Construction and Host Cells

A nucleic acid sequence encoding the amino acid sequence of a therapeutic protein of the invention may be prepared by a variety of methods known in the art. These methods include, but are not limited to, oligonucleotide-mediated (or site-directed) mutagenesis and PCR mutagenesis. A nucleic acid molecule encoding a therapeutic protein of the invention may be obtained using standard techniques, e.g., gene synthesis. Alternatively, a nucleic acid molecule encoding a wild-type therapeutic protein may be mutated to contain specific amino acid substitutions using standard techniques in the art, e.g., QuikChange™ mutagenesis. Nucleic acid molecules can be synthesized using a nucleotide synthesizer or PCR techniques.

Nucleic acid sequences encoding a therapeutic protein of the invention may be inserted into a vector capable of replicating and expressing the nucleic acid molecules in prokaryotic or eukaryotic host cells. Many vectors are available in the art and can be used for the purpose of the invention. Each vector may contain various components that may be adjusted and optimized for compatibility with the particular host cell. For example, the vector components may include, but are not limited to, an origin of replication, a selection marker gene, a promoter, a ribosome binding site, a signal sequence, the nucleic acid sequence encoding protein of interest, and a transcription termination sequence.

In one example, vectors of the invention include: a vector comprising a weak promoter for a selection gene (e.g., 3-ketosteroid reductase and glutamine synthetase) and a strong promoter for the gene encoding the protein of interest (e.g., an antibody, e.g., heavy and light chain of an antibody). Vectors can be linearized or supercoiled exhibiting improved transfection efficiency. In some embodiments, codon optimization of the vector is employed to minimize the use of rare codons in the coding sequence and improve protein production yields. Exemplary vectors of the invention are described in Wurm (2004) Nature Biotechnology, Vol 22; Issue 11: 1393-1398).

In some embodiments, mammalian cells are used as host cells for the invention. The glutamine-auxotrophic and cholesterol-auxotrophic phenotype can be induced by genetic manipulation of a non-glutamine-auxotrophic and non-cholesterol-auxotrophic cell, including for example mutation or deletion of a gene necessary for endogenous glutamine biosynthesis, such as glutamine synthetase. Common methods of genetic engineering are well known to those of skill in the art, e.g., site directed mutagenesis, zinc finger nucleases, shRNA, transposons, See e.g., Cytotechnology. 2007 April; 53(1-3): 65-73. The murine myeloma cells termed NS0 are known glutamine-auxotrophic and cholesterol-auxotrophic cells (See e.g., Barnes et al. Cytotechnology. 2000. *Advances in animal cell recombinant protein production: GS-NS0 expression system February;* 32(2):109-23; and US 20100028940).

Additional examples of mammalian cell types which may be manipulated to be used as host cells include, but are not limited to, human embryonic kidney (HEK) (e.g., HEK293, HEK 293F), Chinese hamster ovary (CHO), HeLa, COS, PC3, Vero, MC3T3, NS0, VERY, BHK, MDCK, W138, BT483, Hs578T, HTB2, BT20, T47D), CRL7030, and HsS78Bst cells. In other embodiments, *E. coli* cells are used as host cells for the invention. Examples of *E. coli* strains include, but are not limited to, *E. coli* 294 (ATCC® 31,446), *E. coli* λ 1776 (ATCC® 31,537, *E. coli* BL21 (DE3) (ATCC® BAA-1025), and *E. coli* RV308 (ATCC® 31,608). Different host cells have characteristic and specific mechanisms for the posttranslational processing and modification of protein products. Appropriate cell lines or host systems may be chosen to ensure the correct modification and processing of the therapeutic protein expressed. The above-described expression vectors may be introduced into appropriate host cells using conventional techniques in the art, e.g., transformation, transfection, electroporation, calcium phosphate precipitation, and direct microinjection. Once the vectors are introduced into host cells for protein production, host cells are cultured in conventional nutrient media modified as appropriate for inducing promoters, selecting transformants, or amplifying the genes encoding the desired sequences. Methods for expression of therapeutic proteins are known in the art, see, for example, Paulina Balbas, Argelia Lorence (eds.) *Recombinant Gene Expression: Reviews and Protocols* (*Methods in Molecular Biology*), Humana Press; 2nd ed. 2004 (Jul. 20, 2004) and Vladimir Voynov and Justin A. Caravella (eds.) *Therapeutic Proteins: Methods and Protocols* (*Methods in Molecular Biology*) Humana Press; 2nd ed. 2012 (Jun. 28, 2012).

Protein Production, Recovery, and Purification

Host cells used to produce a therapeutic protein of the invention may be grown in media known in the art and suitable for culturing of the selected host cells. Examples of suitable media for mammalian host cells include Minimal Essential Medium (MEM), Dulbecco's Modified Eagle's Medium (DMEM), Expi293™ Expression Medium, DMEM with supplemented fetal bovine serum (FBS), and RPMI- 1640. Examples of suitable media for bacterial host cells include Luria broth (LB) plus necessary supplements, such as a selection agent, e.g., ampicillin. Host cells are cultured at suitable temperatures, such as from about 20° C. to about 39° C., e.g., from 25° C. to about 37° C., preferably 37° C., and $CO_2$ levels, such as 5 to 10% (preferably 8%). The pH of the medium is generally from about 6.8 to 7.4, e.g., 7.0, depending mainly on the host organism. If an inducible promoter is used in the expression vector of the invention, protein expression is induced under conditions suitable for the activation of the promoter. Conventional cell culture conditions for production of a therapeutic protein are known in the art, e.g., see Butler, *Cell Culture and Upstream Processing*, Taylor & Francis; 1st edition (May 25, 2007).

Protein recovery typically involves disrupting the host cell, generally by such means as osmotic shock, sonication, or lysis. Once the cells are disrupted, cell debris may be removed by centrifugation or filtration. The proteins may be further purified. An antibody of the invention may be purified by any method known in the art of protein purification, for example, by protein A affinity, other chromatography (e.g., ion exchange, affinity, and size-exclusion column chromatography), centrifugation, differential solubility, or by any other standard technique for the purification of proteins. (see *Process Scale Purification of Antibodies*, Uwe Gottschalk (ed.) John Wiley & Sons, Inc., 2009). In some instances, a therapeutic protein can be conjugated to marker sequences, such as a peptide to facilitate purification. An example of a marker amino acid sequence is a hexa-histidine peptide (His-tag), which binds to nickel-functionalized agarose affinity column with micromolar affinity. Other peptide tags useful for purification include, but are not limited to, the hemagglutinin "HA" tag, which corresponds to an epitope derived from the influenza hemagglutinin protein.

Pharmaceutical Compositions and Preparations

The invention features pharmaceutical compositions that include one or more therapeutic protein described herein. In addition to a therapeutically effective amount of the therapeutic protein, the pharmaceutical compositions may contain one or more pharmaceutically acceptable carriers or excipients, which can be formulated by methods known to those skilled in the art.

Acceptable carriers and excipients in the pharmaceutical compositions are nontoxic to recipients at the dosages and concentrations employed. Acceptable carriers and excipients may include buffers, antioxidants, preservatives, polymers, amino acids, and carbohydrates. Pharmaceutical compositions of the invention can be administered parenterally in the form of an injectable formulation. Pharmaceutical compositions for injection (i.e., intravenous injection) can be formulated using a sterile solution or any pharmaceutically acceptable liquid as a vehicle. Pharmaceutically acceptable vehicles include, but are not limited to, sterile water, physiological saline, and cell culture media (e.g., Dulbecco's Modified Eagle Medium (DMEM), α-Modified Eagles Medium (α-MEM), F-12 medium). Formulation methods are known in the art, see e.g., Banga (ed.) *Therapeutic Peptides and Proteins: Formulation, Processing and Delivery Systems* (2nd ed.) Taylor & Francis Group, CRC Press (2006).

The pharmaceutical composition may be formed in a unit dose form as needed. The amount of active component, e.g., one or more therapeutic protein of the invention included in the pharmaceutical preparations is such that a suitable dose within the designated range is provided (e.g., a dose within the range of 0.01-500 mg/kg of body weight).

Therapeutic Proteins

Therapeutic proteins which may be made by the methods described herein include any recombinant therapeutic protein of interest or biosimilar thereof, including but limited to, antibodies (e.g., monoclonal antibodies, bispecific antibodies, multispecific antibodies), fusion proteins (e.g., Fc fusion), anticoagulants, blood factors, bone morphogenetic proteins, engineered protein scaffolds, enzymes, growth factors, hormones, hormone releasing factors, interferons, interleukins, and thrombolytics. Therapeutic proteins include both glycosylated (e.g., proteins having at least one oligosaccharide chain) and non-glycosylated proteins.

Exemplary monoclonal antibodies include, but are not limited to adalimumab, infiliximab, palivizumab, cetuximab, natalizumab, eculizumab, ustekinumab, golimumab, ofatumab, canakinumab, belimumab, alirocumab, mepolizumab, necitumumab, nivolumab, dinutuximab, secukinumab, evolocumab, blinatumomab, pembrolizumab, ramucirumab, vedolizumab, siltuximab, obinutuzumab, trastuzumab, raxibacumab, pertuzumab, brentuximab, ipilimumab, denosumab, tocilizumab, ofatumumab, canakinumab, certolizumab, catumaxomab, ranibizumab, panitumumab, bevacizumab, cetuximab, efalizumab, omalizumab, tositumomab, ibritumomab, alemtuzumab, gemtuzumab, basiliximab, daclizumab, rituximab, and abciximab.

Exemplary fusion proteins include, but are not limited to alefacept, entanercept, abatacept, belatacept, aflibercept, ziv-aflibercept, rilonacept, romiplostim, apocept, trebananib, blisibimod, and dulaglutide.

Other Embodiments

This invention is further illustrated by the following examples that should not be construed as limiting. The contents of all references, patents and published patent applications cited throughout this application are incorporated herein by reference.

EXAMPLES

Example 1. Manufacture of Therapeutic Antibodies Utilizing a Double Auxotrophic Cell The following Example describes methods of manufacturing therapeutic proteins, such as antibodies, comprising expression of the therapeutic protein of interest in a cholesterol-auxotrophic and glutamine-auxotrophic cell. The method desirably allows for increased amplification and copy number of the gene of interest, and production in the absence of cholesterol, which is highly insoluble in aqueous solutions and very challenging to work with. The exemplary method is further outlined in FIG. 1.

Glutamine-auxotrophic and cholesterol-auxotrophic cells, such as NS0 cells, are transfected with a first vector comprising a nucleic acid encoding a 3-ketosteroid reductase (3-KSR). During and post this first transfection, the cells are maintained in cholesterol-free culture media to select for cells which express the first vector, thereby producing a 3-KSR expressing glutamine-auxotrophic culture of cells. These cells are simultaneously or subsequently transfected with a second vector comprising a nucleic acid encoding a glutamine synthetase (GS) and the protein of interest, e.g., the heavy and light chain of a therapeutic antibody. During and post this second transfection, the cells are maintained in glutamine-free cell culture media to select for cells which express the second vector. To further select for cells which have incorporated multiple copies of the second vector, the cell culture media during and/or after the second transfection is supplemented with a glutamine synthetase inhibitor such as methionine sulfoximine (MSX). The final 3-KSR-GS antibody producing cells can be maintained in a cholesterol-free medium, avoiding cholesterol associated manufacturing problems, and display a high level of productivity derived from the MSX selection.

Example 2. Cell Viability Assay

The following example describes a trypan blue assay to determine cell viability as a proxy for cells that exhibit adequate survival and growth.

Prepare a 0.4% solution of trypan blue in buffered isotonic salt solution, pH 7.2 to 7.3 (i.e., phosphate-buffered saline). Add 0.1 mL of trypan blue stock solution to 1 mL of cells. Load a hemocytometer and examine immediately under a microscope at low magnification. Count the number of blue staining cells and the number of total cells. Cell viability is calculated as the number of viable cells divided by the total number of cells within the grids on the hemocytometer. If cells take up trypan blue, they are considered non-viable. Cell viability is at least 90% for healthy log-phase cultures.

$$\% \text{ viable cells}=[1.00-(\text{Number of blue cells}\div\text{Number of total cells})]\times 100$$

The cell density of the cell line suspension can be determined using a hemocytometer. To calculate the number of viable cells per mL of culture, the following formula is used, correcting for the dilution factor: Number of viable cells×10E4×1.1=cells/mL culture.

Example 3. Manufacture of Therapeutic Antibodies Utilizing a Triple Selection Method The following Example describes methods of manufacturing therapeutic proteins, such as antibodies, comprising expression of the therapeutic protein of interest in a cholesterol- and glutamine-auxotrophic cell with an additional third selection mechanism, e.g., neomycin resistance gene (e.g., using G418 for selection). The method desirably allows for increased amplification and copy number of the gene of interest, and production in the absence of cholesterol, which is highly insoluble in aqueous solutions and very challenging to work with, while overcoming the unexpected manufacturing challenges associated with the 3-KSR cell culture selection system, including for example low productivity.

Figure 9:
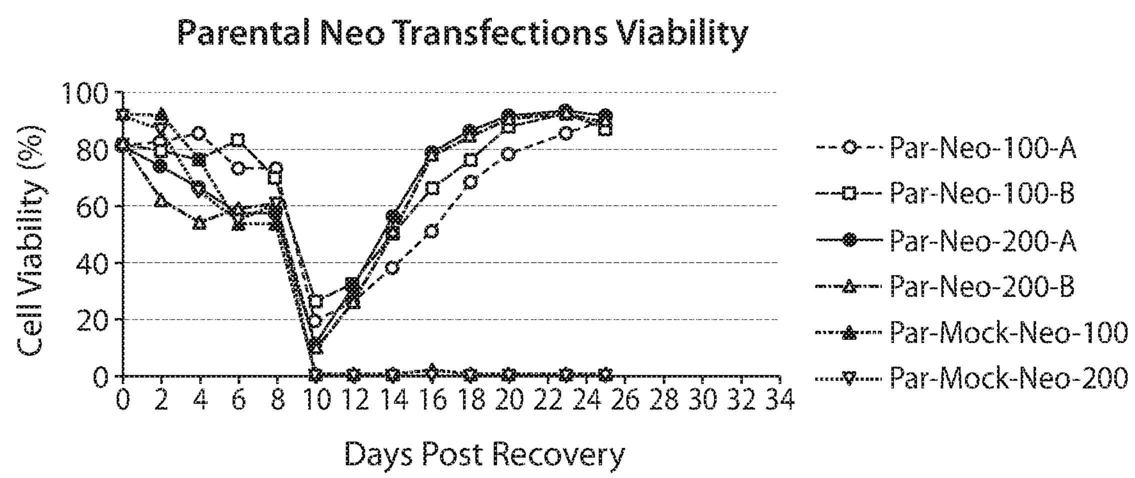
FIG. 9 is a line graph depicting cell selection using Neo (100 μg/ml or 200 μg/ml G418). The graph depicts the cell viability versus days post recovery.
Figure 10:
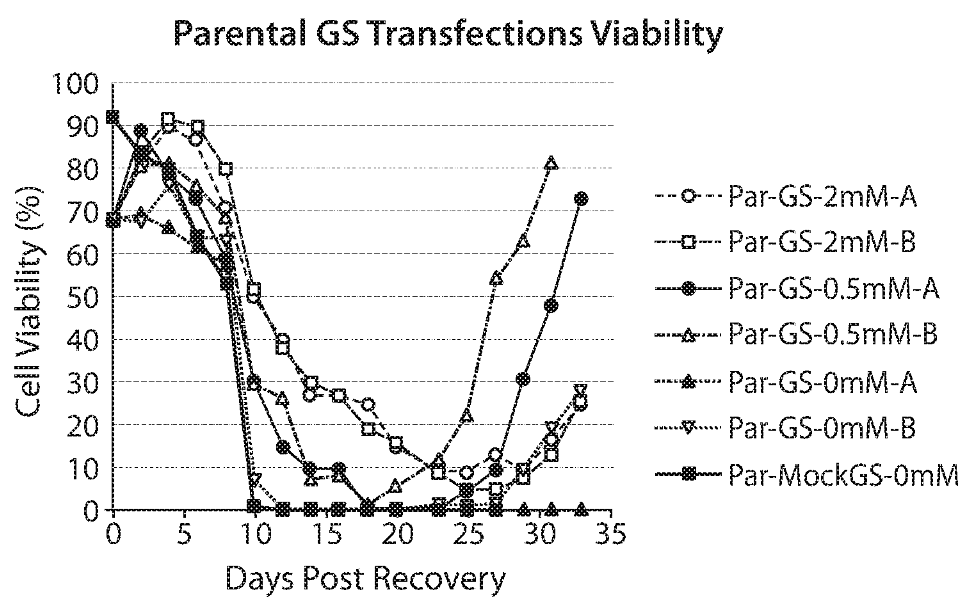
FIG. 10 is a line graph depicting cell selection using glutathione synthetase (GS) (reduce glutamine concentration from 2 mM to 0 mM or from 0.5 mM to 0 mM respectively). The graph depicts the cell viability versus days post recovery.
Figure 11:
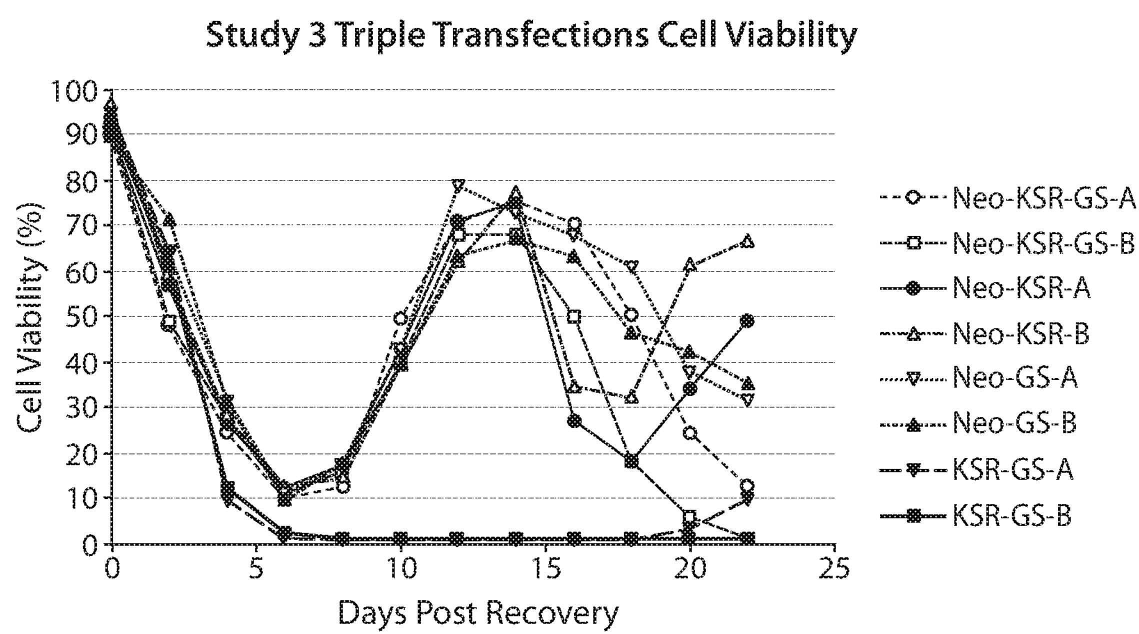
FIG. 11 is a line graph depicting cell selection using 3-KSR, neo, and GS as a triple selection. The graph depicts the cell viability versus days post recovery. Resistance to G418 can be conferred by neo gene. The concentration of G418 in NS0 is 100 ug/ml and 200 ug/ml; reduce glutamine concentration from 2 mM to 0 mM, or from 0.5 mM to 0 mM. An MSX inhibitor may also be used to inhibit the GS activity.

NS0 cell selection was first optimized using both a single neomycin selection (FIG. 9) and a single GS selection (FIG. 10). For neomycin optimization, cells were transfected according to standard practice with a nucleic acid vector encoding a neomycin resistance gene. Neomycin was then added to the cell culture media at either (100 μg/ml or 200 μg/ml) for selection. Cell viability was measured at the denoted days post recovery. For GS based selection, cells were transfected with a nucleic acid vector encoding GS and maintained in glutamine-fee cell culture media. Cell viability was measured at the denoted days post recovery. A 3-KSR based triple selection method was optimized using neomycin, 3-KSR, and GS selection to overcome the unexpectedly low productivity associated with 3-KSR selection (FIG. 8). Cells were transfected according to standard practice with one or more nucleic acid vector encoding 3-KSR, GS, and neomycin resistance gene. For selection, cells were maintained in the absence of glutamine and cholesterol and in the presence of neomycin. As shown in FIG. 11, the triple selection maintained ample cell viability post recovery.

What is claimed:

1. A method of manufacturing a therapeutic protein, comprising: transfecting a mammalian cell which is cholesterol-auxotrophic and glutamine-auxotrophic with (i) a nucleic acid encoding a 3-ketosteroid reductase; (ii) a nucleic acid encoding a glutamine synthetase; (iii) a nucleic acid comprising an aminoglycoside antibiotic resistance gene; and (iv) a nucleic acid encoding the therapeutic protein.

2. The method of claim 1, comprising transfecting the cell with a vector comprising one or more of the following: (i) the nucleic acid encoding the 3-ketosteroid reductase; (ii) the nucleic acid encoding the glutamine synthetase; (iii) the nucleic acid comprising an aminoglycoside antibiotic resistance gene; and (iv) the nucleic acid encoding the therapeutic protein.

3. The method of claim 1, comprising transfecting the cell with a first, a second, and a third vector, wherein the first vector comprises the nucleic acid encoding the 3-ketosteroid reductase; the second vector comprises the nucleic acids encoding the glutamine synthetase; and the third vector comprises the nucleic acid comprising an aminoglycoside antibiotic resistance gene.

4. The method of claim 3, comprising transfecting the cell with the second vector subsequent to or simultaneously with transfecting the cell with the first vector.

5. The method of claim 1, further comprising culturing the cell in the absence of exogenously added cholesterol during or after the transfecting with (i) the nucleic acid encoding the 3-ketosteroid reductase.

6. The method of claim 1, further comprising culturing the cell in the presence of a 3-ketosteroid reductase inhibitor during or after transfecting with (i) the nucleic acid encoding the 3-ketosteroid reductase.

7. The method of claim 1, further comprising culturing the cell in the absence of exogenously added glutamine during or after the transfecting with (ii) the nucleic acid encoding the glutamine synthetase.

8. The method of claim 1, further comprising culturing the cell by gradual reduction of glutamine concentration after the transfecting with (ii) the nucleic acid encoding the glutamine synthetase.

9. The method of claim 8, wherein the glutamine concentration is gradually reduced from 2 mM to 0 mM or from 0.5 mM to 0 mM.

10. The method of claim 1, further comprising culturing the cell in the presence of a glutamine synthetase inhibitor during or after transfecting with (ii) the nucleic acid encoding the glutamine synthetase.

11. The method of claim 1, comprising culturing the cell in the presence of a glutamine synthetase inhibitor during or after transfecting with (ii) the nucleic acid encoding the glutamine synthetase, wherein the glutamine synthetase inhibitor comprises methionine sulfoximine.

12. The method of claim 1, further comprising culturing the cell in the presence of an aminoglycoside antibiotic.

13. The method of claim 12, comprising culturing the cell in the presence of the aminoglycoside antibiotic at a concentration of 100 μg/ml or 200 μg/ml.

14. The method of claim 1, wherein the aminoglycoside resistance gene comprises a neomycin resistance gene and the method comprises transfecting the cell with a nucleic acid that comprises the neomycin resistance gene.

15. The method of claim 1, wherein the cell is maintained in a cholesterol-free culture medium.

16. The method of claim 1, wherein the cell is viable for an extended period of time, post-recovery of the therapeutic protein.

17. The method of claim 16, wherein the extended period of time comprises up to 30 days.

18. The method of claim 1, wherein the therapeutic protein comprises an antibody, a fusion protein, an anticoagulant, a blood factor, a bone morphogenic protein, an engineered protein scaffold, an enzyme, a growth factor, a hormone, a hormone releasing factor, an interferon, an interleukin, or a thrombolytic protein and the method comprises transfecting the cell with a nucleic acid encoding an antibody, a fusion protein, an anticoagulant, a blood factor, a bone morphogenic protein, an engineered protein scaffold, an enzyme, a growth factor, a hormone, a hormone releasing factor, an interferon, an interleukin, or a thrombolytic protein.

19. The method of claim 18, wherein the therapeutic protein comprises the antibody and the method comprises transfecting the cell with a nucleic acid encoding the antibody.

20. The method of claim 18, wherein the therapeutic protein comprises the fusion protein and the method comprises transfecting the cell with a nucleic acid encoding the fusion protein.

21. The method of claim 1, wherein the mammalian cell is an NS0 cell.

22. The method of claim 21, comprising transfecting the NS0 cell with (i) the nucleic acid encoding the 3-ketosteroid reductase; (ii) the nucleic acid encoding the glutamine synthetase; (iii) the nucleic acid comprising an aminoglycoside antibiotic resistance gene, wherein the aminoglycoside antibiotic resistance gene is a neomycin resistance gene, and (iv) a nucleic acid encoding the heavy and light chains of an antibody.

* * * * *

SEQUENCE LISTING

```
<160> NUMBER OF SEQ ID NOS: 7

<210> SEQ ID NO 1
<211> LENGTH: 341
<212> TYPE: PRT
<213> ORGANISM: Homo sapiens

<400> SEQUENCE: 1

Met Arg Lys Val Val Leu Ile Thr Gly Ala Ser Ser Gly Ile Gly Leu
1               5                   10                  15

Ala Leu Cys Lys Arg Leu Leu Ala Glu Asp Asp Glu Leu His Leu Cys
            20                  25                  30

Leu Ala Cys Arg Asn Met Ser Lys Ala Glu Ala Val Cys Ala Ala Leu
        35                  40                  45

Leu Ala Ser His Pro Thr Ala Glu Val Thr Ile Val Gln Val Asp Val
    50                  55                  60

Ser Asn Leu Gln Ser Val Phe Arg Ala Ser Lys Glu Leu Lys Gln Arg
65                  70                  75                  80

Phe Gln Arg Leu Asp Cys Ile Tyr Leu Asn Ala Gly Ile Met Pro Asn
                85                  90                  95

Pro Gln Leu Asn Ile Lys Ala Leu Phe Phe Gly Leu Phe Ser Arg Lys
            100                 105                 110

Val Ile His Met Phe Ser Thr Ala Glu Gly Leu Leu Thr Gln Gly Asp
        115                 120                 125

Lys Ile Thr Ala Asp Gly Leu Gln Glu Val Phe Glu Thr Asn Val Phe
    130                 135                 140
```

```
Gly His Phe Ile Leu Ile Arg Glu Leu Glu Pro Leu Leu Cys His Ser
145                 150                 155                 160

Asp Asn Pro Ser Gln Leu Ile Trp Thr Ser Ser Arg Ser Ala Arg Lys
                165                 170                 175

Ser Asn Phe Ser Leu Glu Asp Phe Gln His Ser Lys Gly Lys Glu Pro
            180                 185                 190

Tyr Ser Ser Ser Lys Tyr Ala Thr Asp Leu Leu Ser Val Ala Leu Asn
        195                 200                 205

Arg Asn Phe Asn Gln Gln Gly Leu Tyr Ser Asn Val Ala Cys Pro Gly
    210                 215                 220

Thr Ala Leu Thr Asn Leu Thr Tyr Gly Ile Leu Pro Pro Phe Ile Trp
225                 230                 235                 240

Thr Leu Leu Met Pro Ala Ile Leu Leu Leu Arg Phe Phe Ala Asn Ala
                245                 250                 255

Phe Thr Leu Thr Pro Tyr Asn Gly Thr Glu Ala Leu Val Trp Leu Phe
            260                 265                 270

His Gln Lys Pro Glu Ser Leu Asn Pro Leu Ile Lys Tyr Leu Ser Ala
        275                 280                 285

Thr Thr Gly Phe Gly Arg Asn Tyr Ile Met Thr Gln Lys Met Asp Leu
    290                 295                 300

Asp Glu Asp Thr Ala Glu Lys Phe Tyr Gln Lys Leu Leu Glu Leu Glu
305                 310                 315                 320

Lys His Ile Arg Val Thr Ile Gln Lys Thr Asp Asn Gln Ala Arg Leu
                325                 330                 335

Ser Gly Ser Cys Leu
            340
```

<210> SEQ ID NO 2
<211> LENGTH: 1537
<212> TYPE: DNA
<213> ORGANISM: Homo sapiens

<400> SEQUENCE: 2

```
gtactctgat tggtgacggg tgaggcggcc cgaaatcgta ggacttccga aagcagcggc      60

ggcgtttgct tcactgcttg gaagtgtgag tgcgcgaaga tgcgaaaggt ggttttgatc     120

accggggcta gcagtggcat tggcctggcc ctctgcaagc ggctgctggc ggaagatgat     180

gagcttcatc tgtgtttggc gtgcaggaac atgagcaagg cagaagctgt ctgtgctgct     240

ctgctggcct ctcaccccac tgctgaggtc accattgtcc aggtggatgt cagcaacctg     300

cagtcggtct tccgggcctc caaggaactt aagcaaaggt ttcagagatt agactgtata     360

tatctaaatg ctgggatcat gcctaatcca caactaaata tcaaagcact tttctttggc     420

ctcttttcaa gaaaagtgat tcatatgttc tccacagctg aaggcctgct gacccagggt     480

gataagatca ctgctgatgg acttcaggag gtgtttgaga ccaatgtctt tggccatttt     540

atcctgattc gggaactgga gcctctcctc tgtcacagtg acaatccatc tcagctcatc     600

tggacatcat ctcgcagtgc aaggaaatct aatttcagcc tcgaggactt ccagcacagc     660

aaaggcaagg aaccctacag ctcttccaaa tatgccactg accttttgag tgtggctttg     720

aacaggaact tcaaccagca gggtctctat tccaatgtgg cctgtccagg tacagcattg     780

accaatttga catatggaat tctgcctccg tttatatgga cgctgttgat gccggcaata     840

ttgctacttc gctttttgc aaatgcattc actttgacac catataatgg aacagaagct      900

ctggtatggc ttttccacca aaagcctgaa tctctcaatc ctctgatcaa atatctgagt     960
```

```
gccaccactg gctttggaag aaattacatt atgacccaga agatggacct agatgaagac   1020

actgctgaaa aattttatca aaagttactg gaactggaaa agcacattag ggtcactatt   1080

caaaaaacag ataatcaggc caggctcagt ggctcatgcc tataattcca gcactttggg   1140

aggccaaggc agaaggatca cttgagacca ggagttcaag accagcctga gaaacatagt   1200

gagcccttgt ctctacaaaa agaaataaaa ataatagctg ggtgtggtgg catgcgcatg   1260

tagtcccagc tactcagaag gatgaggtgg gaggatctct tgaggctggg aggcagaggt   1320

tgcagtgagc tgagattgtg ccactgcact ccagcctggg tgacagcgag accctgtctc   1380

aaaatatgta tatatttaat atatatataa aaccagagct gacaatgaca ctctggaaca   1440

ttgcatacct tctgtacatt ctggggtaca tggatttcta ctgagttgga taatatgcat   1500

ttgtaataaa ctatgaacta tgaaaaaaaa aaaaaaa                            1537
```

<210> SEQ ID NO 3
<211> LENGTH: 373
<212> TYPE: PRT
<213> ORGANISM: Homo sapiens

<400> SEQUENCE: 3

```
Met Thr Thr Ser Ala Ser Ser His Leu Asn Lys Gly Ile Lys Gln Val
1               5                   10                  15

Tyr Met Ser Leu Pro Gln Gly Glu Lys Val Gln Ala Met Tyr Ile Trp
            20                  25                  30

Ile Asp Gly Thr Gly Glu Gly Leu Arg Cys Lys Thr Arg Thr Leu Asp
        35                  40                  45

Ser Glu Pro Lys Cys Val Glu Glu Leu Pro Glu Trp Asn Phe Asp Gly
    50                  55                  60

Ser Ser Thr Leu Gln Ser Glu Gly Ser Asn Ser Asp Met Tyr Leu Val
65                  70                  75                  80

Pro Ala Ala Met Phe Arg Asp Pro Phe Arg Lys Asp Pro Asn Lys Leu
                85                  90                  95

Val Leu Cys Glu Val Phe Lys Tyr Asn Arg Arg Pro Ala Glu Thr Asn
            100                 105                 110

Leu Arg His Thr Cys Lys Arg Ile Met Asp Met Val Ser Asn Gln His
        115                 120                 125

Pro Trp Phe Gly Met Glu Gln Glu Tyr Thr Leu Met Gly Thr Asp Gly
    130                 135                 140

His Pro Phe Gly Trp Pro Ser Asn Gly Phe Pro Gly Pro Gln Gly Pro
145                 150                 155                 160

Tyr Tyr Cys Gly Val Gly Ala Asp Arg Ala Tyr Gly Arg Asp Ile Val
                165                 170                 175

Glu Ala His Tyr Arg Ala Cys Leu Tyr Ala Gly Val Lys Ile Ala Gly
            180                 185                 190

Thr Asn Ala Glu Val Met Pro Ala Gln Trp Glu Phe Gln Ile Gly Pro
        195                 200                 205

Cys Glu Gly Ile Ser Met Gly Asp His Leu Trp Val Ala Arg Phe Ile
    210                 215                 220

Leu His Arg Val Cys Glu Asp Phe Gly Val Ile Ala Thr Phe Asp Pro
225                 230                 235                 240

Lys Pro Ile Pro Gly Asn Trp Asn Gly Ala Gly Cys His Thr Asn Phe
                245                 250                 255

Ser Thr Lys Ala Met Arg Glu Glu Asn Gly Leu Lys Tyr Ile Glu Glu
            260                 265                 270
```

```
Ala Ile Glu Lys Leu Ser Lys Arg His Gln Tyr His Ile Arg Ala Tyr
        275                 280                 285

Asp Pro Lys Gly Gly Leu Asp Asn Ala Arg Arg Leu Thr Gly Phe His
    290                 295                 300

Glu Thr Ser Asn Ile Asn Asp Phe Ser Ala Gly Val Ala Asn Arg Ser
305                 310                 315                 320

Ala Ser Ile Arg Ile Pro Arg Thr Val Gly Gln Glu Lys Lys Gly Tyr
                325                 330                 335

Phe Glu Asp Arg Arg Pro Ser Ala Asn Cys Asp Pro Phe Ser Val Thr
            340                 345                 350

Glu Ala Leu Ile Arg Thr Cys Leu Leu Asn Glu Thr Gly Asp Glu Pro
        355                 360                 365

Phe Gln Tyr Lys Asn
    370


<210> SEQ ID NO 4
<211> LENGTH: 8337
<212> TYPE: DNA
<213> ORGANISM: Homo sapiens

<400> SEQUENCE: 4

gtaaaactat tccccgtgaa ggcggcaggg cagaggtcca gggcgggctt tgctgggagc     60

ctcgggaccc cgggttgggg gccgtggggc ggcacctggc gagctggcgg gtgggcggcg    120

agccgaggct tcccggcctg gcggcaactc gcccctctgc cctcagccct cccggctccg    180

ctcccttccc ccacgccgcc ctgcccctcc cccacgcccc tttctctttc tttctttctt    240

tcccagttcg cttgccccca ccccagcggc gcccgccggg ctcctcgccc aatggccgcg    300

gggcccggga ccgcatcagc tgatcggccc gggctcctgg ccgctgggag ccaatcaggg    360

caccgggggc ggcccccggc cgcggataaa gggtgcgggg ctgctggcgg ctctgcagag    420

tcgagagtgg gagaagagcg gagcgtgtga gcagtactgc ggcctcctct cctctcctaa    480

cctcgctctc gcggcctagc tttacccgcc cgcctgctcg gcgaccagcg gggatcctcc    540

cccagccgca agtccacgaa gaaagcaacg aatgaaaatt atgaagacaa cgagaagtca    600

gactcctccg ggtcgcgctc cagctgcttc ggcttcgtcg cctactctgt gaactccggg    660

gagagatctc gagtcaagat taagacctta acccaccaac ctgcctgttc ggacaccccc    720

cgggccggcc gctgtctgtc cccttctcca tcgccctctc ccagaaagct ccggtgcttg    780

gaccagctag agtctgagaa agaggagagg cgcgaacgcc actccaaaaa gagaagggtt    840

aaagagggca accctaacga tacgcttgac tttctgtggc tgggaacacc ttccaccatg    900

accacctcag caagttccca cttaaataaa ggcatcaagc aggtgtacat gtccctgcct    960

cagggtgaga aagtccaggc catgtatatc tggatcgatg gtactggaga aggactgcgc   1020

tgcaagaccc ggaccctgga cagtgagccc aagtgtgtgg aagagttgcc tgagtggaat   1080

ttcgatggct ctagtacttt acagtctgag ggttccaaca gtgacatgta tctcgtgcct   1140

gctgccatgt ttcgggaccc cttccgtaag gaccctaaca agctggtgtt atgtgaagtt   1200

ttcaagtaca atcgaaggcc tgcagagacc aatttgaggc acacctgtaa acggataatg   1260

gacatggtga gcaaccagca cccctggttt ggcatggagc aggagtatac cctcatgggg   1320

acagatgggc accccttttgg ttggccttcc aacggcttcc cagggcccca gggtccatat   1380

tactgtggtg tgggagcaga cagagcctat ggcagggaca tcgtggaggc ccattaccgg   1440

gcctgcttgt atgctggagt caagattgcg gggactaatg ccgaggtcat gcctgcccag   1500
```

-continued

```
tgggaatttc agattggacc ttgtgaagga atcagcatgg gagatcatct ctgggtggcc   1560
cgtttcatct tgcatcgtgt gtgtgaagac tttggagtga tagcaacctt tgatcctaag   1620
cccattcctg ggaactggaa tggtgcaggc tgccatacca acttcagcac caaggccatg   1680
cgggaggaga atggtctgaa gtacatcgag gaggccattg agaaactaag caagcggcac   1740
cagtaccaca tccgtgccta tgatcccaag ggaggcctgg acaatgcccg acgtctaact   1800
ggattccatg aaacctccaa catcaacgac ttttctgctg gtgtagccaa tcgtagcgcc   1860
agcatacgca ttccccggac tgttggccag gagaagaagg gttactttga agatcgtcgc   1920
ccctctgcca actgcgaccc ctttttcggtg acagaagccc tcatccgcac gtgtcttctc   1980
aatgaaaccg gcgatgagcc cttccagtac aaaaattaag tggactagac ctccagctgt   2040
tgagcccctc ctagttcttc atcccactcc aactcttccc cctctcccag ttgtcccgat   2100
tgtaactcaa agggtggaat atcaaggtcg tttttttcat tccatgtgcc cagttaatct   2160
tgctttcttt gtttggctgg gatagagggg tcaagttatt aatttcttca cacctaccct   2220
cctttttttc cctatcactg aagcttttta gtgcattagt ggggaggagg gtggggagac   2280
ataaccactg cttccattta atggggtgca cctgtccaat aggcgtagct atccggacag   2340
agcacgtttg cagaaggggg tctcttcttc caggtagctg aaaggggaag acctgacgta   2400
ctctggttag gttaggactt gccctcgtgg tggaaacttt tcttaaaaag ttataaccaa   2460
cttttctatt aaaagtggga attaggagag aaggtagggg ttgggaatca gagagaatgg   2520
ctttggtctc ttgcttgtgg gactagcctg gcttgggact aaatgccctg ctctgaacac   2580
gaagcttagt ataaactgat ggatatccct accttgaaag aagaaaaggt tcttactgct   2640
tggtccttga tttatcacac aaagcagaat agtatttttta tatttaaatg taaagacaaa   2700
aaactatatg tatggttttg tggattatgt gtgttttgct aaaggaaaaa accatccagg   2760
tcacggggca ccaaatttga gacaaatagt cggattagaa ataaagcatc tcattttgag   2820
tagagagcaa gggaagtggt tcttagatgg tgatctggga ttaggccctc aagacccttt   2880
tgggtttctg ccctgcccac cctctggaga aggtgggcac tggattagtt aacagacaac   2940
acgttactag cagtcacttg atctccgtgg ctttggttta aaagacacac ttgtccacat   3000
aggtttagag ataagagttg gctggtcaac ttgagcatgt tactgacaga gggggtattg   3060
gggttatttt ctggtaggaa tagcatgtca ctaaagcagg ccttttgata ttaaattttt   3120
taaaaagcaa aattatagaa gtttagattt taatcaaatt tgtagggttt ctaggtaatt   3180
tttacagaat tgcttgtttg cttcaactgt ctcctacctc tgctcttgga ggagatgggg   3240
acagggctgg agtcaaaaca cttgtaattt tgtatcttga tgtctttgtt aagactgctg   3300
aagaattatt ttttttcttt tataataagg aataaacccc acctttattc cttcatttca   3360
tctaccattt tctggttctt gtgttggctg tggcaggcca gctgtggttt tcttttgcca   3420
tgacaacttc taattgccat gtacagtatg ttcaaagtca aataactcct cattgtaaac   3480
aaactgtgta actgcccaaa gcagcactta taaatcagcc taacataaga tctctctgat   3540
gtgtttgtga ttctttcaaa tccctatgtg ccattatatt tctttatttc ctaaaacagg   3600
caaaataagc tcaagtttat gtactctgag tttttaaaac actggagtga tgttgctgac   3660
cagccgtttc ctgtacctct ctaagttggg tatttgggac ttaagggatt aagtttttca   3720
cctagactta gttacacaca atcttggcat ttcctagcct agaggtttgt agcagggtac   3780
aagccccact cctccccctt cctttgctcc cctgagtttg gttttggctt accataacat   3840
```

```
tgttttgacc attcctagcc taatacaata gcctaacata atgtaagatt aactggcttt   3900
acgatttcta ttctctgctc tcagtgataa gaaacaaata ttagctaccc tgctaccctg   3960
gttgaagcct tccaaggctg gctatgccct aggcatgggc tcatccttgg gtgtatcttg   4020
ccttgcagga agaccagtgg accgattgtg attctcaaaa gctctgtgtt gtcacctgtg   4080
cccttgcccc ttgctcttat cttggtccgt gtatctggga gttcttccac cttatcttgg   4140
ccaattccta ccttcgttca ttcctcatga ggttgggtaa aagctccctc cggctcccat   4200
gatgctgtgc atatacctag caaaaagcaa ttattggaca cattggagtg caatattatt   4260
aatagcatta atactactaa taatgtgggc aatagtgatt gtttttaaaa ggcagtatac   4320
tcttaccagt gcgaggtagc tggggcctgt gatagttttt agagataagt tcttcaggca   4380
actgtgtatt ttacactagt caagtaatcc tagatatccg tggtttttct taagaaagtt   4440
ggctcgtaat atgatttaat attcaaagta gagtcatcta cctattagct tgctggcgtg   4500
gtcctagttt atgcctgttt cagcatgatt gttgagtacc ctgtttcatc cttagcattt   4560
tcttgatttt gttgttaaat gatgtatacc cttatttcca ttgaatctgt gcttccaccc   4620
ccccaactga agttgtcttc cctttgcttg gccaccctta cagcctcttg gatggtgtat   4680
cctacagtgt aagcactaaa ctgaagaggc agtgacctga gcactttgga ttttgttcat   4740
tgtaatcaat tccatgacaa aatgattgca tgagaaggaa ttttaaattc ataggatcag   4800
aatttaggtg aaaacaacca gcatatttgt ttcttcaccc tctcacctag aattagcttt   4860
gacctacagg tcacagtgca atccccttgt atttctaagg tgttttttat agttcatttg   4920
cagacaatgg gttatgtgat aacttttatc agtgatagat taaacagaat aatgaccaag   4980
ctttcaacct taaggagtca ggccagtatt tacaaaagga ggtctccatg aactccttaa   5040
atatgagttc ccctaatatc atcttgccag gtactaaata acaactgata gcacaagcta   5100
tagggaattt gaaagaattc catggatggg tgttgtctag ggccttttgt tgtttttgag   5160
acggggtctg actctcaccc aggctggagt atagtgtggc gcaatcttgg ctcactgcaa   5220
cttctgcctc ccagattcaa gcgattctcc tgcctcagcc tcccaagtag ctgagactac   5280
aggtgtgcac caccatgctc agctaatttt tgtattttta gtacagatgg ggtttcacca   5340
tgttggccag gctggtcttg aactcctgat ctcccaaagt gaggtcttga actggtcttg   5400
aactcctcca cctcccaaag tgctgggatt acaggcgtga gccactgcac ccggcctagg   5460
gccatgtaaa aagccagatc tgtgctgctg tctgtgtaga agggtagaca agtggatgag   5520
aagttcctga actattcttg gccctttac cactaagtga aagtaacttg ctgccccaaa    5580
gaaagatgtc tcatcattcg acaggacttt ctagttgaac ttcatgaaag caagagatcc   5640
tgtttttctt gctcaccact gtatcttgag acctgttgta gtgcctgcaa tacttattta   5700
ataagttatt tttaagtatc agttttgtga gctttaactc tatgaggtct ttgttgtttg   5760
actgtatttt aactctggcc atgacagcaa gacaaagttc catttttatt gagcttaaaa   5820
agaatcaagg ccaggtgaag tggcttacgc ctgtgatccc aacactttgt gaggctgcag   5880
caggaggatc tcttgagccc aggagtttga gaccgttcta ggcaatgtag tgaggtccag   5940
actccacaaa ataatttttt tttaaattgc acgcctgtag tctcagctat caggaggctg   6000
agatgggagg atgacttgag cccaggaaat tgaagctgca gtgaattgtg attgcaccac   6060
tgcactccag cctgggtgac agatcaagac cttgcctaaa caaaacaaaa caaacaaaac   6120
cccaaaaaac aaattgaaaa tgttgattct ttttactaca aacattatgg cagcactaaa   6180
aacttcgtgg gagtgtactg tggaaaatag tgtacttaat taattctcat tgtaatcagg   6240
```

-continued

```
ctaccaagag ccttgtgttg ctttaagagt tataactgcc aggcacagtg gctcatgcct   6300
ataatcccag caccttgaga ggccgaggca ggtggatcac ctgagatcgg gagtttgaga   6360
ccagccgggc caatatggtg aaacaagctg tgtctctact aaatacaaaa aattagccgg   6420
gcgtggtggc acatgcctgt aatcccagct gcttgggaga ctgagacagg agaattgctt   6480
gaacctggaa ggcggaggtt gcagtgagct gagattgcaa cattgtactc cagcctgggc   6540
aacaagaggg aaactccatc tcaaaaaaaa aaaaaaagtt gtaactgagg ctgggcatgg   6600
tggctcatac ctgtaatccc agcactttga aaagccgagg caggtagatc acttgagctc   6660
agaagttcga gactagcctg ggcaacatga caaaacccca tctctacaaa aaatacgaaa   6720
aattagctgg gcgtggtggc atgcacctgt agtcctagct acctgggagg ctgaggtggg   6780
aagattactt gaagctgcag tgagccatgg ttgtgccact gccctccagt ctgggcaaca   6840
aagtgagacc ctgtctcaaa aaaacaaaaa aaaattataa ctgatgtaaa ctggcagttt   6900
aggctgggtg tggtggctca agcctgtaat cctagcactt tgggaggcca aggcaggtgg   6960
atcacctgag ttcaggagtt cgagaccagc gtggccaaca tggtgaaacc ttgtctctat   7020
taaaaatacc aaaattagca agatgtggtg gtgggtgcct ataattccag ctactcagga   7080
ggctgaggca ggaggatcgc tggagccagg gaggcagagg ttacagtaag caaagatcac   7140
tccacttcac tccagcctgg gcaaaagagt gagacatatc aaaaaataaa caaataaata   7200
aataaataag tggcagttca tcatttaact ccaaagactt tgcgtacatt tctactgaaa   7260
acaatctgag ctgattagaa ccctgccatt ttatagcctt tagctcgatc tccgaccgtt   7320
catttaaaaa aattctactt caggccgggc atggtggctc aagcctgtaa tcccatcact   7380
gtaggaggcc aaagtgggca gatcacttaa ggtcaggagt ttgagaccag cctggccacc   7440
atggtgaaac cccatctcta ctaaaaatac aaaaattagc cgggcttggt ggtgagcacc   7500
tgtaatccca ccctgccgag tggcaggctg aggcaggaga atcgcttgag cccaagagcc   7560
ggaggttgca gtgagccaag cttgcaccat tgcactccag cctaggcaac agagtgtgac   7620
tccatctcaa gaaaaaaaaa attctatttc attttacaat atgcagatat atgtccatac   7680
acatgcataa tataaatgta taccatattt gtgagaatat gcatatatgt acacattaga   7740
tacacaatac aagcacaata catatgtctt ttgcccaaga tacagcattt tgtaaaggag   7800
acaggaattt agtaatatat gttccagaaa cagtacacaa gagaattcgc cgagatgaga   7860
aagttgtcac taggaatggg gagtggtaag atgtagaagg tataattgtt cttaaagttc   7920
tactgccaac tctttccaat taattaccca ctctgccatg ctttatggac aggaggttgt   7980
cggacactgt caattaataa atatttgagc atgatacact gcttggagct cctctaatat   8040
aggagagtga tatcctagtg catgttacag agggagtgtc cacacagttc ctattgtcat   8100
ttgatgagtt acttttcagg ggccttgtac ctgagcaagt tgtcctcttt ttgatggatt   8160
tcagattgag ttacctgcat tgtcttgaga ttgcagcgtg tttcctccac tgtacggcgt   8220
agtcagcaga tctattagtt aaactccagt gggccctcag tcactaaatc tatcctctgt   8280
gttgaaggct ttctgcattt gcctttcaat aaaggtttag aataactcct taaaaaa      8337
```

<210> SEQ ID NO 5
<211> LENGTH: 187
<212> TYPE: PRT
<213> ORGANISM: Homo sapiens

<400> SEQUENCE: 5

-continued

```
Met Val Gly Ser Leu Asn Cys Ile Val Ala Val Ser Gln Asn Met Gly
1               5                   10                  15

Ile Gly Lys Asn Gly Asp Leu Pro Trp Pro Pro Leu Arg Asn Glu Phe
            20                  25                  30

Arg Tyr Phe Gln Arg Met Thr Thr Thr Ser Ser Val Glu Gly Lys Gln
        35                  40                  45

Asn Leu Val Ile Met Gly Lys Lys Thr Trp Phe Ser Ile Pro Glu Lys
    50                  55                  60

Asn Arg Pro Leu Lys Gly Arg Ile Asn Leu Val Leu Ser Arg Glu Leu
65                  70                  75                  80

Lys Glu Pro Pro Gln Gly Ala His Phe Leu Ser Arg Ser Leu Asp Asp
                85                  90                  95

Ala Leu Lys Leu Thr Glu Gln Pro Glu Leu Ala Asn Lys Val Asp Met
            100                 105                 110

Val Trp Ile Val Gly Gly Ser Ser Val Tyr Lys Glu Ala Met Asn His
        115                 120                 125

Pro Gly His Leu Lys Leu Phe Val Thr Arg Ile Met Gln Asp Phe Glu
    130                 135                 140

Ser Asp Thr Phe Phe Pro Glu Ile Asp Leu Glu Lys Tyr Lys Leu Leu
145                 150                 155                 160

Pro Glu Tyr Pro Gly Val Leu Ser Asp Val Gln Glu Glu Lys Gly Ile
                165                 170                 175

Lys Tyr Lys Phe Glu Val Tyr Glu Lys Asn Asp
            180                 185
```

<210> SEQ ID NO 6
<211> LENGTH: 3932
<212> TYPE: DNA
<213> ORGANISM: Homo sapiens

<400> SEQUENCE: 6

```
tcccagacag aacctactat gtgcggcggc agctggggcg ggaaggcggg agctgggggc      60

gctgggggcg ctgcggccgc tgcggccgct gcagccgctg cagcgccagg gtccacctgg     120

tcggctgcac ctgtggagga ggaggtggat ttcaggcttc ccgtagactg gaagaatcgg     180

ctcaaaaccg cttgcctcgc aggggctgag ctggaggcag cgaggccgcc cgacgcaggc     240

ttccggcgag acatggcagg gcaaggatgg cagcccggcg gcagggcctg gcgaggagcg     300

cgagcccgcg gccgcagttc ccaggcgtct gcgggcgcga gcacgccgcg accctgcgtg     360

cgccggggcg ggggggcggg gcctcgcctg cacaaatggg gacgaggggg gcggggcggc     420

cacaatttcg cgccaaactt gaccgcgcgt tctgctgtaa cgagcgggct cggaggtcct     480

cccgctgctg tcatggttgg ttcgctaaac tgcatcgtcg ctgtgtccca gaacatgggc     540

atcggcaaga acggggacct gccctggcca ccgctcagga atgaattcag atatttccag     600

agaatgacca caacctcttc agtagaaggt aaacagaatc tggtgattat gggtaagaag     660

acctggttct ccattcctga gaagaatcga cctttaaagg gtagaattaa tttagttctc     720

agcagagaac tcaaggaacc tccacaagga gctcattttc tttccagaag tctagatgat     780

gccttaaaac ttactgaaca accagaatta gcaaataaag tagacatggt ctggatagtt     840

ggtggcagtt ctgtttataa ggaagccatg aatcacccag gccatcttaa actatttgtg     900

acaaggatca tgcaagactt tgaaagtgac acgtttttc cagaaattga tttggagaaa      960

tataaacttc tgccagaata cccaggtgtt ctctctgatg tccaggagga gaaaggcatt    1020

aagtacaaat ttgaagtata tgagaagaat gattaatatg aaggtgtttt ctagtttaag    1080
```

```
ttgttccccc tccctctgaa aaaagtatgt atttttacat tagaaaaggt tttttgttga   1140
ctttagatct ataattattt ctaagcaact agtttttatt ccccactact cttgtctcta   1200
tcagatacca tttatgagac attcttgcta taactaagtg cttctccaag accccaactg   1260
agtccccagc acctgctaca gtgagctgcc attccacacc catcacatgt ggcactcttg   1320
ccagtccttg acattgtcgg gcttttcaca tgttggtaat atttattaaa gatgaagatc   1380
cacataccct tcaactgagc agtttcacta gtggaaatac caaaagcttc ctacgtgtat   1440
atccagaggt ttgtagataa atgttgccac cttgtttgta acagtgaaaa attgaaaaca   1500
acctggaagt ccagtgatgg gaaaatgagt atgtttctgt cttagattgg ggaacccaaa   1560
gcagattgca agactgaaat ttcagtgaaa gcagtgtatt tgctaggtca taccagaaat   1620
catcaattga ggtacggaga aactgaactg agaaggtaag aaaagcaatt taaagtcagc   1680
gagcaggttc tcattgataa caagctccat actgctgaga tacagggaaa tggagggggg   1740
aaagctggag tattgatccc gcccccctcc ttggttgtca gctccctgtc ctgtgtgtgg   1800
gcggaacata gtccagctgc tctatagcaa gtctcaggtg tttgcagtaa gaagctgctg   1860
gcatgcacgg gaacagtgaa tgccaaacac ttaaagcaat tcgatgttta agtatgtaag   1920
ttcttttttt tttagacagc gtttcgctct tgttgcccag gctagcatgc aatggtgtga   1980
cctcggctta ctgcaacctc cgccttccca gattcaagcg attctcctgc ctcaggctcc   2040
caagtagcta ggaccaggtg cgcgccacca cgcccggcta atttttgtat tttgtatttt   2100
tagtagagat ggggtttcac catgttggtc aggctagtct cgaactcgtg accgcaagcg   2160
attcacccac ctcagcctcc caaagtgctg ggattaccgg cttgagccac cacacccggc   2220
acatcttcat tctttttatg tagtaaaaag tataaggcca cacatggttt atttgaagta   2280
ttttataatt taaaaaaata cagaagcagg aaaaccaatt ataagttcaa gtgagggatg   2340
atggttgctt gaaccaaagg gttgcatgta gtaagaaatt gtgatttaag atatatttta   2400
aagttataag tagcaggata ttctgatgga gtttgacttt ggttttgggc ccagggagtt   2460
tcagatgcct ttgagaaatg aatgaagtag agagaaaata aaagaaaaac cagccaggca   2520
cagtggctca cacctgtaat cccagcgctt tgggaggcta aggcaggcag atcacttgag   2580
accagcttgg gcaacatggc aaagccccat ctctacaaaa aacacaaaaa ttagctgggc   2640
attgtggcgc acacctgtat tcccatctag tcaggaagct gagatggaag aattaattga   2700
gcccacgagt tcaaggctgc agtgagtcgt gattgtgcca ctgcactcca gccggggtga   2760
cagaagagac cttgtctcga aaaggaatct gaaaacaatg gaaccatgcc ttcataattc   2820
tagaaagtta ttttcaactg ataaatctat attcacccaa ataatcaagg gtgaaggtaa   2880
aataatacat ttttagacaa gcaaagactc aggggttacc tccatgtgcc ctttttaggg   2940
aagctgttgg agaaaatact ccagcaaaat gaaggagtac acaaaccaga gaatgacatg   3000
aatccagcaa ataggatcca acacaggcaa tattccagct atggagctag ctttaaaaag   3060
gaacagtaaa aatattaatc ggttagctgg gtggaatggc ccatgcctgt agtcccagct   3120
actcaggagg ctcagcagca ggacgacttg agcccaagag ttccagacca gcctggccac   3180
cttagtgaga tcccttctct taaaaataat aacttattgc cagatttggg gcatttggaa   3240
agaagttcat tgaagataaa gcaaaagtaa aaaaaaaaaa aaaaaaaaca aggggaaagg   3300
gttggttagg caatcattct agggcagaaa gaagtacagg ataggaagag cataatacac   3360
tgtttttctc aacaaggagc agtatgtaca cagtcataat gatgtgactg cttagcccct   3420
```

-continued

```
aaatatggta actactctgg gacaatatgg gaggaaaagt gaagattgtg atggtgtaag   3480

agctaaatcc tcatctgtca tatccagaaa tcactatata atatataata atgaaatgac   3540

taagttatgt gaggaaaaaa acagaagaca ttgctaaaag agttaaaagt cattgctctg   3600

gagaattagg agggatgggg caggggactg ttaggatgca ttataaactg aaaagccttt   3660

ttaaaatttt atgtattaat atatgcattc acttgaaaaa ctaaaaaaaa acaataattt   3720

ggaaaaaccc atgaaggtaa ctaacggaag gaaaaactaa gagaatgaaa agtatttgcc   3780

tctggaaaga acaactggca ggactgttgt tttcattgta agacttttgg agccatttaa   3840

ttgtacttaa ccattttcat ctatttcttt aataagaaca attccatctt aataaagagt   3900

tacacttgtt aataagtaaa aaaaaaaaaa aa                                  3932


<210> SEQ ID NO 7
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 7

His His His His His His
1               5
```